US008118761B2

(12) United States Patent
Rogachevsky

(10) Patent No.: US 8,118,761 B2
(45) Date of Patent: Feb. 21, 2012

(54) SYSTEM AND METHOD FOR TEMPORO-MANDIBULAR JOINT DECOMPRESSION DURING CERVICAL TRACTION

(76) Inventor: Richard J. Rogachevsky, Honolulu, HI (US)

(*) Notice: Subject to any disclaimer, the term of this patent is extended or adjusted under 35 U.S.C. 154(b) by 141 days.

(21) Appl. No.: 11/388,898

(22) Filed: Mar. 24, 2006

(65) Prior Publication Data

US 2006/0217647 A1    Sep. 28, 2006

Related U.S. Application Data

(60) Provisional application No. 60/664,830, filed on Mar. 24, 2005, provisional application No. 60/737,833, filed on Nov. 16, 2005.

(51) Int. Cl.
*A61F 5/37* (2006.01)
*A61F 5/00* (2006.01)
*A61B 19/00* (2006.01)
*A61H 1/00* (2006.01)
*A61H 1/02* (2006.01)
*A61H 5/00* (2006.01)
*A61H 7/00* (2006.01)
*A61H 19/00* (2006.01)

(52) U.S. Cl. .............. 602/18; 602/5; 602/12; 602/13; 602/19; 602/32; 128/846; 128/869; 128/873; 128/874; 601/39; 601/148; 601/149; 601/150; 601/151; 601/152

(58) Field of Classification Search .............. 602/13, 602/17–18, 32; 24/300, 324, 701; 601/11, 601/39, 148–152; 128/845, DIG. 20, DIG. 23
See application file for complete search history.

(56) References Cited

U.S. PATENT DOCUMENTS

| 2,102,069 | A | 12/1937 | Hanike |
| 3,892,229 | A | 7/1975 | Taylor |
| 3,942,518 | A | 3/1976 | Tenteris et al. |
| 4,099,523 | A | 7/1978 | Lowrey |
| 4,715,362 | A | 12/1987 | Scott |
| 4,745,922 | A | 5/1988 | Taylor |
| 5,600,136 | A | 2/1997 | Hablanian et al. |
| 5,752,927 | A | 5/1998 | Rogachevsky |

(Continued)

FOREIGN PATENT DOCUMENTS

DE    2129140    12/1972

(Continued)

OTHER PUBLICATIONS

Chiropractic Products, Advertisement for Traction Units by Meditrac Ltd., Sep. 2005, p. 47.
Chiropractic Economics Buyer's Guide, Advertisement for Portable Cervical Traction by Oriental Neck Therapy, 2004, p. 52, vol. 49, Issue 16.

(Continued)

*Primary Examiner* — Patricia Bianco
*Assistant Examiner* — Brandon Jackson
(74) *Attorney, Agent, or Firm* — Paul F. Rusyn; Graybeal Jackson LLP

(57) ABSTRACT

Traction devices, systems, and methods for their use provide simultaneous axial distraction and one of flexion, extension, or lateral flexion of the spine. The devices permit aligning at least a portion of the spine prior to traction. Traction is applied through air chambers configured and dimensioned to independently apply traction to the chin, and both occipital processes. Spiral traction procedures use sequential inflation of the air chambers, thereby providing axial distraction with spinal joint decompression and simultaneous paraspinal soft-tissue mobilization and/or manipulation. Automated systems and methods are also provided.

31 Claims, 31 Drawing Sheets

U.S. PATENT DOCUMENTS

| | | | |
|---|---|---|---|
| 5,916,185 A | | 6/1999 | Chitwood |
| 6,050,965 A | | 4/2000 | Pillai |
| 6,319,180 B1 | | 11/2001 | Kallassy |
| 6,458,090 B1 | * | 10/2002 | Walpin ............... 602/18 |
| 6,719,713 B2 | * | 4/2004 | Mason ............... 602/26 |
| 7,062,794 B2 | * | 6/2006 | LeBlanc ............... 2/312 |
| 2002/0066454 A1 | * | 6/2002 | Kittelsen et al. ............... 128/859 |
| 2003/0120192 A1 | | 6/2003 | Chao |
| 2006/0015048 A1 | | 1/2006 | Pillai |
| 2006/0217648 A1 | | 9/2006 | Rogachevsky |

FOREIGN PATENT DOCUMENTS

| | | |
|---|---|---|
| DE | 3318938 | 11/1984 |
| DE | 9000599 | 9/1990 |
| DE | 29613213 | 10/1996 |
| EP | 0784968 | 7/1997 |
| WO | WO-9507669 A1 | 3/1995 |
| WO | WO-99-03440 | 1/1999 |

OTHER PUBLICATIONS

Rolyan Chiropractic Equipment and Supplies, Advertisement for Pneu-Trac®, Fall 2004, p. 74.

Chiropractic Products 2002-03 Buyer's Guide, Advertisement for Posture Pump®—Spine Trainer®, p. 9.

American 3B Scientific 2004 Medical & Patient Education and Therapy Catalog, Advertisement for Sauders Clinical Cervical Traction Device, p. 170.

Pronex Pneumatic Cervical Traction Device Study, Journal of the Neuromusculoskeletal System, 1995, 82-91, vol. 3.

Chiropractic Products 2002-03 Buyer's Guide, Jun. 2003, Advertisement for Cervical Over Door Traction, p. 31.

"U.S. Appl. No. 11/388,336, Non-Final Office Action mailed Jan. 22, 2010", 14 pgs.

Erin L. Elster, "Upper Cervical Chiropractic Management of a Multiple Sclerosis Patient: A case Report", J. Vertebral subluxation Res., 4(2), 2001 pp. 22-30.

\* cited by examiner

SYSTEM AND METHOD FOR TEMPORO-MANDIBULAR JOINT DECOMPRESSION DURING CERVICAL TRACTION

CROSS-REFERENCE TO RELATED APPLICATIONS

This application claims the benefit of U.S. Application No. 60/664,830, filed Mar. 24, 2005 and U.S. Application No. 60/737,833, filed Nov. 16, 2005, the disclosures of which are incorporated by reference in their entireties. This application is also related to U.S. application Ser. No. 11/388,336, filed concurrently with the present application, which is incorporated by reference in its entirety.

BACKGROUND OF THE INVENTION

1. Field of the Invention

This disclosure generally relates to treatment of the spine, and more particularly to devices, systems, and methods for simultaneous axial distraction, and one of flexion, extension, or lateral flexion of the spine.

2. Description of the Related Art

A clinical study of cervical traction devices (Patrick P. Venditti, et al., J *Neuromusculoskeletal Sys.* 1995, 3(2):82-91, the disclosure of which is incorporated by reference) has been found to separate the articular surfaces of the cervical vertebral joints, thereby increasing the spinal-disc height. None of the tested devices relaxed the neck muscles.

SUMMARY OF THE INVENTION

Traction devices, systems, and methods for their use provide simultaneous axial distraction and one of flexion, extension, or lateral flexion of the spine. The devices permit aligning at least a portion of the spine prior to traction. Traction is applied through air chambers configured and dimensioned to independently apply traction to the chin, and both occipital processes. Spiral traction procedures use sequential inflation of the air chambers, thereby providing axial distraction with spinal joint decompression and simultaneous paraspinal soft-tissue mobilization and/or manipulation. Automated systems and methods are also provided.

Accordingly, some embodiments provide a cervical traction system comprising a C-shaped inflatable, four-chamber cervical collar comprising: a front and a back, a right end and a left end defining a back opening; a bottom section comprising an inflatable bottom chamber in fluid connection with a first tubing port; a top section disposed on the bottom section; and a releasable closure for closing the back opening between the right end and the left end. The top section comprises: an inflatable right rear chamber in fluid connection with a second tubing port, wherein the right rear chamber is disposed towards a right end of the top section, an inflatable left rear chamber in fluid connection with a third tubing port, wherein the left rear chamber is disposed towards a left end of the top section, and an inflatable front chamber in fluid connection with a fourth tubing port. The front chamber is disposed between the right rear chamber and the left rear chamber, and a chin cup disposed at a front end of the front chamber.

In some embodiments, the releasable closure comprises a plurality of straps and corresponding pegs. Each peg comprises a shank and an enlarged head. Each strap comprises: a first end and a second end; a plurality of openings extending from the first end toward the second end, wherein each opening comprises a larger portion proximal to the second end and a smaller portion proximal to the first end; the larger portion is sized and dimensioned to pass over the enlarged head of the peg; and the smaller portion is sized and dimensioned to accept the shank, but not to pass over the enlarged head of the peg. The second end of the strap is secured to one of the right end or left end of the collar, extending toward the opening, and the corresponding peg is secured to the other of the right end or left end of the collar.

Some embodiments further comprise a first front strap securing the front chamber to the right rear chamber; and a second front strap securing the front chamber to the left rear chamber.

In some embodiments, the chin cup is permanently coupled to the front chamber. In some embodiments, the chin cup is generally boomerang-shaped, comprising a pair of arms converging at a point; the point is disposed at the front of the collar; and the chin cup is sized and dimensioned such that the point is positioned under a user's chin and the arms extend about halfway to the angle of the mandible.

Some embodiments further comprise a right and a left temporomandibular joint spacer, each temporomandibular joint spacer comprising an inner wall, an upper wall, and an outer wall defining a channel, wherein the channel is sized and configured to cover at least partially the biting surface of at least one of the user's molars or premolars.

Some embodiments further comprise a gas manifold in fluid connection with the tubing ports of the bottom chamber, the right rear chamber, the left rear chamber, and the front chamber; and a source of pressurized gas for influx into the gas manifold.

Also provided is a method for simultaneous axial distraction, and at least one of flexion, extension, and lateral flexion of a user's neck comprising: securing the cervical collar of claim 1 to the neck of a patient; inflating the bottom chamber to contact the chin cup with the user's chin; inflating the right and left rear chambers to contact right and left occipital regions of the user's head; applying cervical traction by sequential inflation of at least two of the top section chambers; deflating at least one of the top section chambers; and optionally repeating applying cervical traction.

In some embodiments, the sequential inflation comprises at least one of the following inflation sequences: a first sequence comprising left rear, right rear, both rear, and front; a phase-shifted variant thereof; and the reverse of the first sequence or phase-shifted variant.

In some embodiments, the sequential inflation comprises at least one of the following inflation sequences: a second sequence comprising left rear, both rear, right rear, front; a phase-shifted variant thereof; or the reverse of the second sequence or phase-shifted variant.

Also provided is a neck-and-upper-back frame system for cervical traction on a user comprising: a top and a bottom; a front and a back; a left side and a right side; a neck frame; and a shoulder frame comprising right and left shoulder pads sized and dimensioned for simultaneously engaging a user's right and left shoulders, respectively, wherein each shoulder pad comprises a front end and a back end defining a longitudinal axis, and the neck frame is coupled to the shoulder frame, and the neck frame's position with respect to the shoulder frame is adjustable. The neck frame comprises: a plurality of lockably slidable slats; an inflatable front chamber sized and dimensioned to engage a user's chin, and coupled to at least one of one of the slats; an inflatable right rear chamber sized and dimensioned to engage the right occipital region the user's head, and coupled to at least one of the slats; and an inflatable left rear chamber sized and dimensioned to engage the left occipital region the user's head, and coupled to at least one of the slats, wherein the plurality of slats is slidably adjustable for simultaneous engagement of the front chamber to the user's chin, the right rear chamber to the right occipital region of the user's head, and the left rear chamber to the left occipital region of the user's head.

In some embodiments, the neck frame is swivelably coupled to the shoulder frame. In some embodiments, each shoulder pad comprises an inflatable shoulder chamber positioned to contact the user's shoulder.

Some embodiments further comprise an upper-back frame operatively coupled to the back ends of the shoulder pads, wherein the upper-back frame comprises: an inflatable right upper-back chamber sized and dimensioned to contact a user's right upper back; and an inflatable left upper-back chamber sized and dimensioned to contact a user's left upper back, wherein the upper-back frame and shoulder frame together are securable to the user.

In some embodiments, the sliding of at least one of the slats is lockable using a slat sleeve comprising a plunger sized and dimensioned to engage an opening in the slat-to-be-locked.

In some embodiments, the plurality of slats comprises: a left lateral slat and a right lateral slat generally defining right and left sides of a rectangle; and a rear slat and a front slat generally defining rear and front sides of the rectangle; a right occipital cup comprising the right rear chamber is coupled to the rear slat; a left occipital cup comprising the left rear chamber is coupled to the rear slat; and a chin cup comprising the front chamber is coupled to the front slat. Some embodiments further comprise: a right slat sleeve coupled to the right shoulder pad; and a left slat sleeve coupled to the left shoulder pad, wherein the right lateral slat is slidably coupled in the right slat sleeve; the left lateral slat is slidably coupled in the left slat sleeve; and the sliding of the lateral slat in at least one of the left slat sleeve or the right slat sleeve is lockable.

In some embodiments, a height of at least one of the right occipital cup, the left occipital cup, or the chin cup is user adjustable. In some embodiments, a sagittal tilt of at least one of the right occipital cup, the left occipital cup, or the chin cup is adjustable.

In some embodiments, the neck frame is lockably slidable forward and backward relative to the shoulder frame. In some embodiments, the neck frame is coupled to a right tilting lever and a left tilting lever, the right tilting lever is lockably slidable along the longitudinal axis of the right shoulder pad, and the left tilting lever is lockably slidable along the longitudinal axis of the left shoulder pad.

In some embodiments, the neck frame is lockably pivotable relative to the shoulder frame around a transverse axis. In some embodiments, the neck frame is coupled to a right slat sleeve and a left slat sleeve; the right slat sleeve is coupled to the right shoulder pad and is lockably pivotable around the transverse axis; and the left slat sleeve is coupled to the left shoulder pad and is lockably pivotable around the transverse axis.

In some embodiments, the front chamber is generally boomerang-shaped, comprising a pair of arms converging at a point; the point is disposed at the front of the chin cup; and the front chamber is sized and dimensioned such that the point is positioned under a user's chin and the arms extend about halfway to the angle of the mandible.

Some embodiments further comprise a right and a left temporomandibular joint spacer, each temporomandibular joint spacer comprising an inner wall, an upper wall, and an outer wall defining a channel, wherein the channel is sized and configured to cover at least partially the biting surface of at least one of the user's molars or premolars.

Some embodiments further comprise a gas manifold in fluid connection with the front chamber, the right rear chamber, and the left rear chamber; and a source of pressurized gas for influx of gas into the manifold.

Also provided is a neck-and-upper-back frame system comprising: a means for simultaneous axial distraction, and one of flexion, extension, or lateral flexion of a user's spine; and a means for aligning a user's upper back, wherein the distraction means is swivelably coupled to the alignment means.

Also provided is a method for simultaneous axial distraction, and one of flexion, extension, or lateral flexion of a user's spine comprising: securing a disclosed neck-and-upper-back frame system to a patient; slidably adjusting the plurality of slats to simultaneously engage the front chamber to the user's chin, the right rear chamber to the right occipital region of the user's head, and the left rear chamber to the left occipital region of the user's head; applying cervical traction by sequential inflation of the front chamber, right rear chamber, left rear chamber, or a combination thereof; deflating the front chamber, right rear chamber, and left rear chamber; and optionally repeating applying cervical traction.

In some embodiments, the sequential inflation comprises at least one of the following inflation sequences: a second sequence comprising left rear, both rear, right rear, front; a phase-shifted variant thereof; or the reverse of the second sequence or phase-shifted variant. In some embodiments, the sequential inflation comprises at least one of the following inflation sequences: a second sequence comprising left rear, both rear, right rear, front; a phase-shifted variant thereof; or the reverse of the second sequence or phase-shifted variant.

Some embodiments further comprise at least one of extending, rotating, or laterally flexing the thoracic spine prior to applying cervical traction by inflating at least one of a right upper back chamber or a left upper back chamber. Some embodiments further comprise stretching the user's trapezius muscles prior to applying cervical traction by inflating a right shoulder chamber and a left shoulder chamber. In some embodiments, the inflation of the front chamber, right rear chamber, and left rear chamber is automated.

DETAILED DESCRIPTION OF THE PREFERRED EMBODIMENTS

Embodiments of disclosed devices, systems, and methods exhibit at least some of the following features, which are discussed in greater detail below. Embodiments of the devices are portable, compact, lightweight, and easily assembled and disassembled. Accordingly, they are suitable for both clinical and home use. Embodiments of devices permit the neck to be oriented in any position (rotation, flexion, extension, side extension) prior to traction. Traction of the neck and upper back uses up to seven points of contact. The neck traction uses spiral pathways (spiral traction). Aligning the upper-thoracic spine reduces thoracic kyphosis (hunched posture), internal rotation of the shoulders (rounded shoulders), and/or upper-thoracic rotational scoliosis. Temporo-mandibular joints (TMJs) are decompressed. The traction uses a low traction force.

Figure 1A:
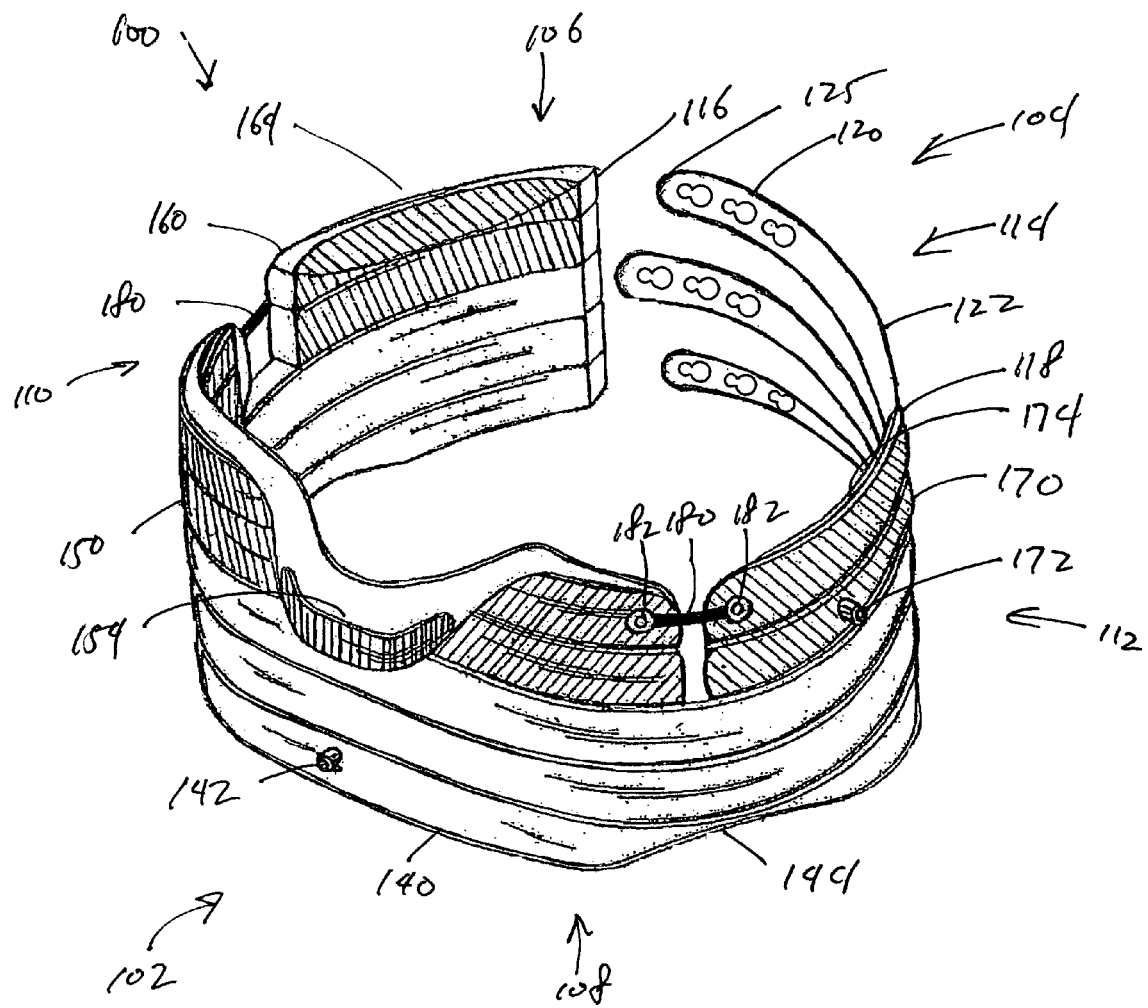
FIG. 1A illustrates in perspective an embodiment of an inflatable four-chamber collar.

FIG. 1A illustrates in perspective an embodiment of an inflatable four-chamber collar 100 comprising a front 102, a back 104, a top section 106, a bottom section 108, a right side 110, and a left side 112. The collar 100 is generally C-shaped, with an opening 114 at the back 104. The opening 114 is defined by a first or right end 116, and a second or left end 118. The opening 114 permits a user to position the collar 100 around the neck. As will become apparent below, providing the opening 114 in the back provides a unitary traction force on the user's chin, rather than a divided force, which would result from a front-opening device. Moreover, it is difficult to equalize the divided force in some embodiments of a front opening device, resulting in an off center force. Some embodiments of the collar 100 are supplied in a range of sizes, for example, to accommodate different neck sizes in adults and children.

The illustrated collar 100 comprises four air chambers, each of which is independently inflatable and deflatable. In some embodiments, each chamber comprises sub-chambers in fluid connection. The bottom section 108 comprises a bottom chamber 140 extending from the first end 116 and the second end 118. The bottom chamber 140 serves as a platform for a top section 106, which comprises upper air chambers which may include a front chamber 150 disposed in the front 102 of the collar 100, a right rear chamber 160 and a left rear chamber 170 adjacent the front chamber 150. In some embodiments, the length of the front chamber 150 is from about ⅓ to about ½ of the total length of the upper section 106. In the illustrated embodiment, the front chamber 150 does not contact either the right 160 or left 170 rear chamber, and is independently secured to each using front straps 180. In the illustrated embodiment, the front straps 180 are secured using rivets 182. Those skilled in the art will understand that the other embodiments use other fastening means known in the art, for example, adhesives, laces, hooks, stitching, screws, bolts, pins, hook-and-loop fasteners, combinations, and the like. In some embodiments, at least one end of a front strap 180 is secured to an outer layer, which is discussed in greater detail below. In preferred embodiments, one or both ends of the front straps 180 have at least some rotational freedom of motion, thereby accommodating the relative motion of the air chambers as they are inflated and/or deflated. In other embodiments, the front chamber 150 contacts at least one of the right 160 and/or left 170 rear chambers.

The air chambers comprise any suitable material. In general, at least one of the materials is flexible and airtight. In some embodiments, at least one of the materials is elastic, and expandable, for example, natural rubber, synthetic rubber, elastomeric polymers, elastomeric fabrics, elastomeric fibers, combinations, and the like. Other embodiments do not use an elastic and/or expandable material. In some embodiments, the air chambers comprise a composite, for example, a fabric impregnated with and/or laminated with a polymer and/or rubber. In some preferred embodiments, the air chambers comprise a polymer, for example, polyvinyl chloride (PVC). In some embodiments, the air chambers comprise a single material. In other embodiments, one or more of the air chambers comprises a plurality of materials. In the illustrated embodiment, each air chamber comprises accordion-type pleating or corrugations, which permit the air chambers to expand and contract vertically as each is inflated and deflated. In other embodiments, only some or none of the air chambers comprises pleating.

In some embodiments, at least a portion of an air chamber is disposed in and/or covered by one or more outer layers, which, for example, constrains the shape of the air chamber during inflation and/or deflation, and/or protects the air chamber, for example, providing puncture resistance. The outer layer(s) comprises one or more materials that provide desired properties. For example, in some embodiments, portions of the cover likely to contact a user's skin comprise a wicking material. In some embodiments, the outer layer forms a bag and/or cover in which the air chambers are disposed.

The bottom chamber 140 comprises a tubing port 142 through which the bottom chamber 140 is inflated and/or deflated. The bottom chamber further comprises left and right cutouts 144 (only the left cutout is visible in FIG. 1A) sized and dimensioned to engage a user's upper trapezius (shoulder) area.

The left rear chamber 170 comprises a tubing port 172 through which the left rear chamber 170 is inflated and/or deflated. A left occipital support 174 is provided to engage the left occipital region of the head. In the illustrated embodiment, the left occipital support 174 is a cutout in the left rear chamber 170 sized and dimensioned to engage the left occipital region of the head.

The right rear chamber 160 comprises a tubing port 162 (not visible in FIG. 1A) through which the right rear chamber 160 is inflated and/or deflated. A right occipital support 164 is provided to engage the right occipital region of the head. In the illustrated embodiment, the right occipital support 164 is a cutout in the right rear chamber 170 sized and dimensioned to engage the right occipital region of the head.

Figure 1B:
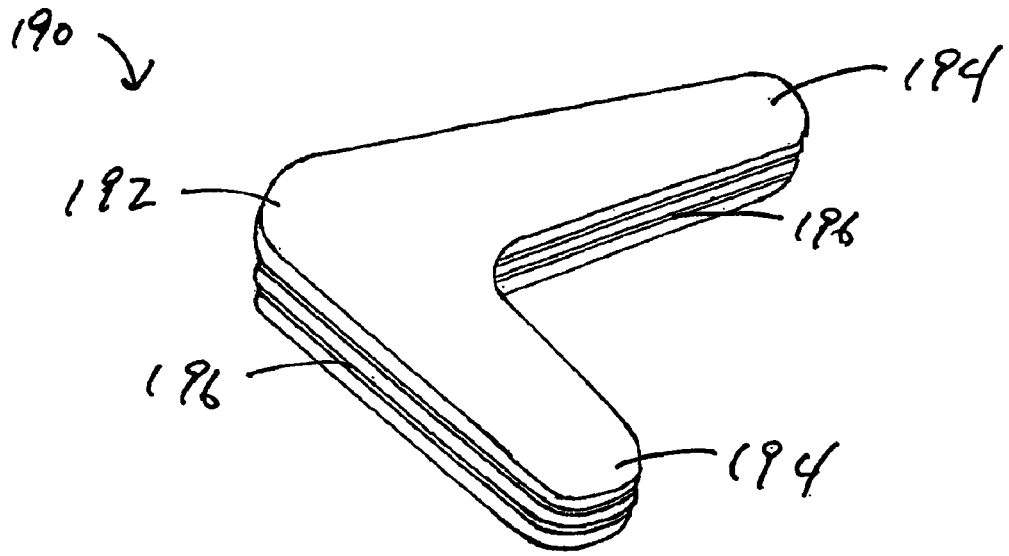
FIG. 1B illustrates a perspective view of an embodiment of a chin cup.

The front chamber 150 also comprises a tubing port (not visible in FIG. 1A) through which the front chamber 150 is inflated and/or deflated. A cutout 154 is formed in the front of the front chamber 150 that is sized and dimensioned to cradle and support a user's chin. A chin cup 190 (not visible in FIG. 1A) is secured in the cutout 154. A preferred embodiment of the chin cup 190 is best viewed in FIG. 1B. The illustrated chin cup 190 is generally boomerang-shaped with a point 192 formed at the intersection of a pair of arms 194. The chin cup 190 comprises a flexible outer shell, which preferably comprises a polymer. Corrugations or pleats 196 are provided on the sides of the chin cup 190, which accommodate height changes as the chin cup 190 is compressed and released. In some embodiments, a compressible fill material and/or fluid fill material is provided in the interior of the chin cup 190. In the illustrated embodiment, the chin cup 190 is substantially permanently secured to the cutout 154. In other embodiments, the chin cup 190 is removably secured, for example, to change the size of the chin cup. Undesirable movement of the chin cup 190 occurs in some embodiments in which the chin cup 190 is removable. Accordingly, in some preferred embodiments, the chin cup 190 is permanently secured.

The point 192 generally points forward in the cutout 154, and supports the chin. The arms 194 are positioned below the mandible. In the illustrated embodiment, each arm 194 extends from the front of a user's chin to about half the distance to the angle of the mandible. Accordingly, a range of sizes of chin cups 190 accommodate different jaw sizes in some embodiments. The thickness of the illustrated chin cup 190 is from about 1 cm (about 0.4") to about 4 cm (about 1.6"), preferably from about 2 cm (about 0.8") to about 3 cm (about 1.2"). Those skilled in the art will understand that other dimensions and/or shapes are useful in other embodiments. In other embodiments, chin cup 190 integrally formed in the cutout 154.

The collar 100 is fastened around the neck of a user using fastening and/or closure means 120 known in the art, for example, using straps, buttons, laces, D-rings, slide fasteners (zippers), hook-and-loop fasteners (Velcro®), buckles, clasps, hooks, combinations, and the like. In some embodiments, at least one of the fasteners is secured to one or more of the air chambers. In some embodiments, at least one of the fasteners is secured to an outer layer described above. In some embodiments, the fasteners are not secured to the collar 100, for example, straps encircling the collar 100. In some preferred embodiments, the fastening means 120 are adjustable, thereby permitting the user to adjust the fit of the collar 110. The embodiment illustrated in FIG. 1A includes a preferred fastening means 120 comprising a plurality of straps 122 secured proximal to the left end 118 of the collar, and corresponding pegs, rivets, and/or buttons 130, which are not illustrated in FIG. 1A, secured proximal to the right end 116 of the collar. In the illustrated embodiment, two each of the straps 122 and pegs 130 are secured to the bottom chamber 140, and one strap 122 and peg 130 are secured to the left 170 and right 160 rear chambers, respectively. Those skilled in the art will understand that, in other embodiments, the positions of one or more of the straps 122 and pegs 130 are reversed, for example, to provide left and right-handed models of the collar 100. Other embodiments use a different number and/or configuration of straps and pegs.

Figure 1C:
FIGS. 1C and 1D illustrate embodiments of a closure comprising a peg in side view and a strap in top view, respectively.

FIG. 1C is a side view of a peg, rivet, or button 130 comprising a shank 132 secured proximal to the right end 116 of the collar and an enlarged head 134. In some embodiments, the peg 130 is substantially cylindrically symmetric, while in other embodiments, the peg 130 is not cylindrically symmetric. The shank 132 of the peg is secured to the right end 116 collar using any means known in the art, for example, using a rivet, screw, bolt, pin, stitching, adhesive, combinations, and the like. The peg 130 comprises any suitable material, for example, a metal, ceramic, inorganic materials, biological materials, and/or polymer. Composites, some of which are fiber reinforced, are also suitable.

Figure 1D:
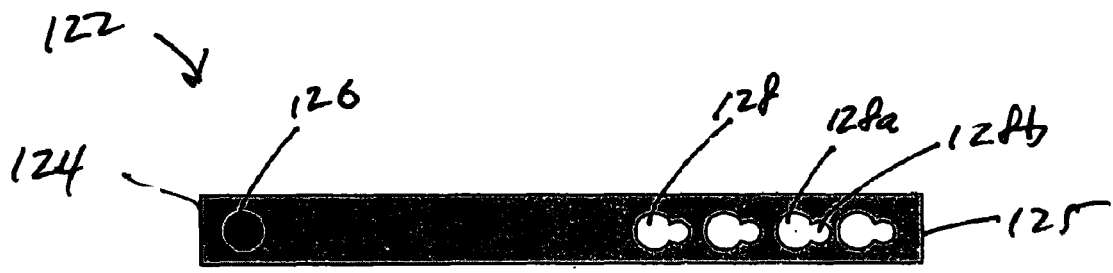

FIG. 1D is a top view of a strap 122, which comprises first end 124 proximal to the left end 118 of the collar, and a second end 125, which extends toward the right end 116 of the collar in the illustrated embodiment. The strap 122 is secured to the left end 118 using a fastener 126 of any suitable type known in the art, for example, a rivet, screw, bolt, pin, stitching, adhesive, combinations, and the like. In preferred embodiments, the fastener 126 permits the strap 122 at least a degree of rotational freedom, which permits some relative motion during inflation and/or deflation of the air chambers. The illustrated embodiment further comprises a plurality of openings 128, each of which has a larger portion 128a proximal to the first end 124, and a smaller portion 128b proximal to the second end 125. The larger portion 128a is dimensioned and sized to pass over the enlarged head 134 of the peg. The smaller portion 128b is dimensioned and sized to accommodate the shank 132 of the peg, but not to pass over the enlarged head 134. The plurality of openings 128 provides a range of sizes for the collar 100. In some embodiments, at least a portion of the opening 128 is reinforced, for example, using a grommet, by stitching, and/or using other means known in the art. The strap 122 comprises any suitable material, for example, leather, fabric, polymer, combinations, and the like. In some embodiments, the material is a composite, which is fiber and/or fabric reinforced in some embodiments.

In use, the collar 100 is positioned around a user's neck with the opening 114 facing backwards. The user selects an opening 128 on each strap that provides the desired fit, and passes the larger portion 128a of the opening over the enlarged head 134 of the corresponding button 130. In the illustrated embodiment, the straps 122 and pegs 130 cooperatively secure the collar 100 to the user with reduced rates of slipping and/or failure. Inflating the air chambers in the collar 100 causes expansion of both the height and diameter of the collar 100. Increasing the diameter applies tension to the straps 122, thereby causing the shank 132 to lodge in the smaller portion 128b of the opening. Because the head 134 of the button is larger than the smaller portion 128b of the opening, the closure resists slipping.

As discussed above, the fastener(s) 120 provide a degree of adjustability in the diameter of the collar 120. In some preferred embodiments, the collar 100 is provided in a plurality of diameters, for example, small, medium, and large for adults to accommodate a range of neck sizes. Some embodiments of the collar 100 are also sized for children. In the cillustrated embodiment, the bottom section 108 is from about ⅓ to about ⅔ of the total height of the collar 100, more preferably, about ½ of the total height of the collar 100 in the uninflated state. On inflation, the height of the collar 100 increases to a maximum of from about 125% to about 500% of the uninflated height, preferably, from about 200% to about 300%. In some embodiments, the widths of different portions of the collar 100 are different, for example, wider under the chin cup 190 and/or at the cut outs, 164 and 174. The maximum inflated width of the collar 100 is from about 125% to about 200% of the uninflated width. Those skilled in the art will understand that the inflation characteristics of each air chamber are individually selectable according the particular application. For example, in some embodiments, the different air chambers have different maximum inflation sizes as a percentage of the uninflated size. Moreover, those skilled in the art will understand that some embodiments of the air chambers inflate anisotropically, for example, the change in height is different from the change in width as a percentage of the uninflated size.

Tubing ports are each fluidly connected to one or more sources of a pressurized gas. In preferred embodiments, each of the tubing ports 142, 152, 162, and 172 is fluidly connected to a manifold, which in preferred embodiments, permits the use of a single source of pressurized gas. The manifold fluidly connects the tubing ports 142, 152, 162, and/or 172 to a source of pressurized gas or to the ambient atmosphere, thereby permitting the independent inflation and deflation of the corresponding air chambers 140, 150, 160, and 170, respectively. Suitable manifolds are known in the art. In some embodiments, the manifold is manually controlled. In preferred embodiments, the manifold is under automatic control, for example, using a computer, microprocessor, or the like. In some embodiments, the source of pressurized gas is user generated, for example, a hand bulb, foot pump, user operated pump, or the like. In preferred embodiments, the source of pressurized gas is not user generated, for example, a mechanical pump or a compressed gas cylinder. In some embodiments, the speed of inflation and/or deflation of each air chamber is independently controllable. In some embodiments, at least two, and preferably all, of the tubing ports 142, 152, 162, and 172 are disposed on a single connector that permits a simple, one step connection of all of the tubing ports 142, 152, 162, and 172 to the manifold. In some embodiments, the connector is designed to prevent improper connection. In some embodiments, the connector is a quick release connector.

Figure 2:
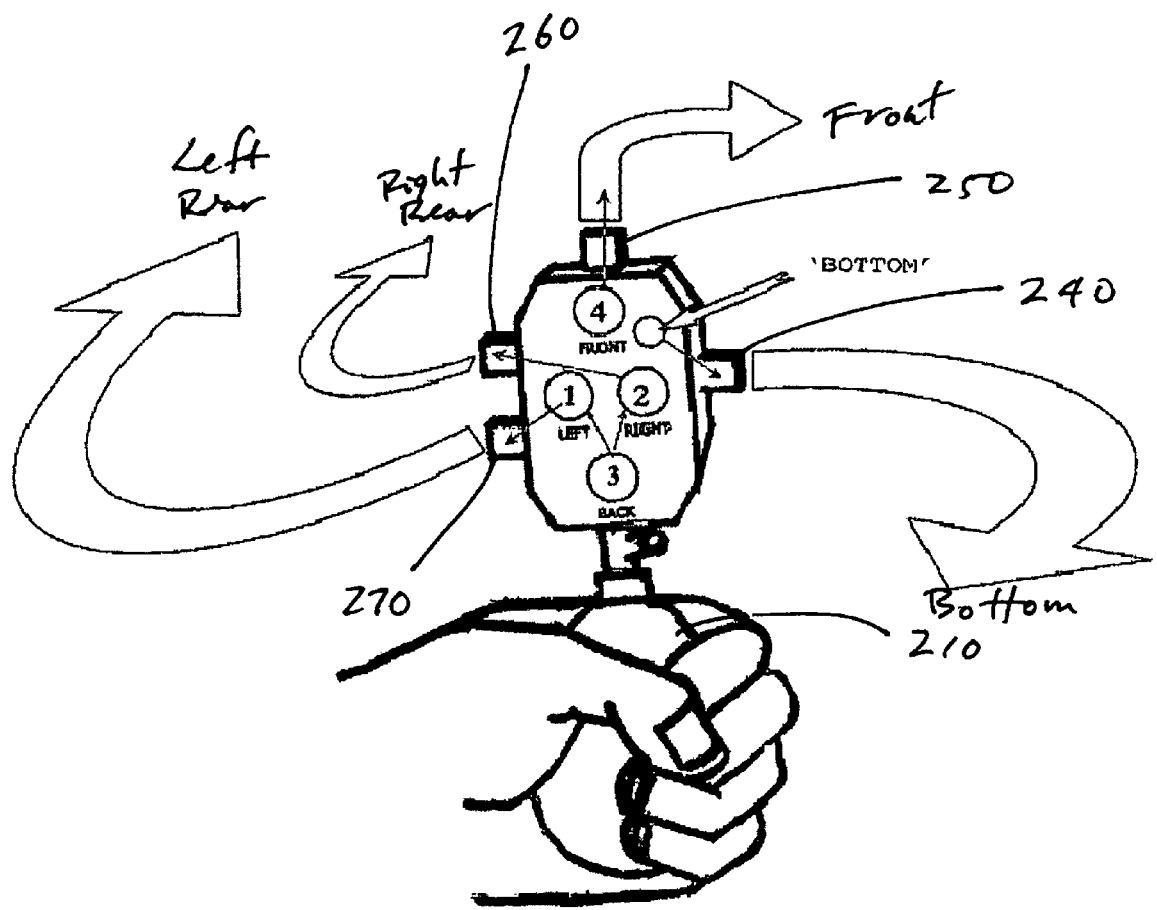
FIG. 2 illustrates in perspective view an embodiment of a manually operated manifold and gas bulb.

FIG. 2 illustrates an embodiment of an embodiment of a user operated manifold or air shunting valve 200 comprising a plurality of tubing ports, each of which corresponds to an air chamber of the collar 100. Port 240 is fluidly connected to the tubing port 142 of the bottom chamber. Port 250 is fluidly connected to the tubing port 152 of the front chamber. Port 260 is fluidly connected to the tubing port 162 of the right rear chamber. Port 270 is fluidly connected to the tubing port 172 of the left rear chamber. Connections are made using tubing, for example, rubber, PVC, or other tubing known in the art. In the illustrated embodiment, pressurized gas is provided using a hand bulb 210. The manifold 200 comprises valves that selectively and independently fluidly connect each port or a combination thereof with either the hand bulb 210, or with ambient pressure. The valve labeled "1" controls port 270, and consequently, the inflation and deflation of the left rear chamber 170. The valve labeled "2" controls port 260, and consequently, the inflation and deflation of the right rear chamber 160. The valve labeled "3" controls ports 260 and 270, and consequently, the inflation and deflation of both the right 160 and left 170 rear chambers. The valve labeled "4" controls port 250, and consequently, the inflation and deflation of the front chamber 150. The valve labeled "Bottom" controls port 240, and consequently, the inflation and deflation of the bottom chamber 140. Some embodiments also comprise one or more quick release valves that release the pressure from one or more of the air chambers (not illustrated), for example, in a slow and controlled manner. The quick release valve in some preferred embodiments release the pressure from the top section 106 (front, left rear, and right rear) air chambers. Some embodiments comprise a quick release valve that releases the pressure from all four air chambers.

Figure 3:
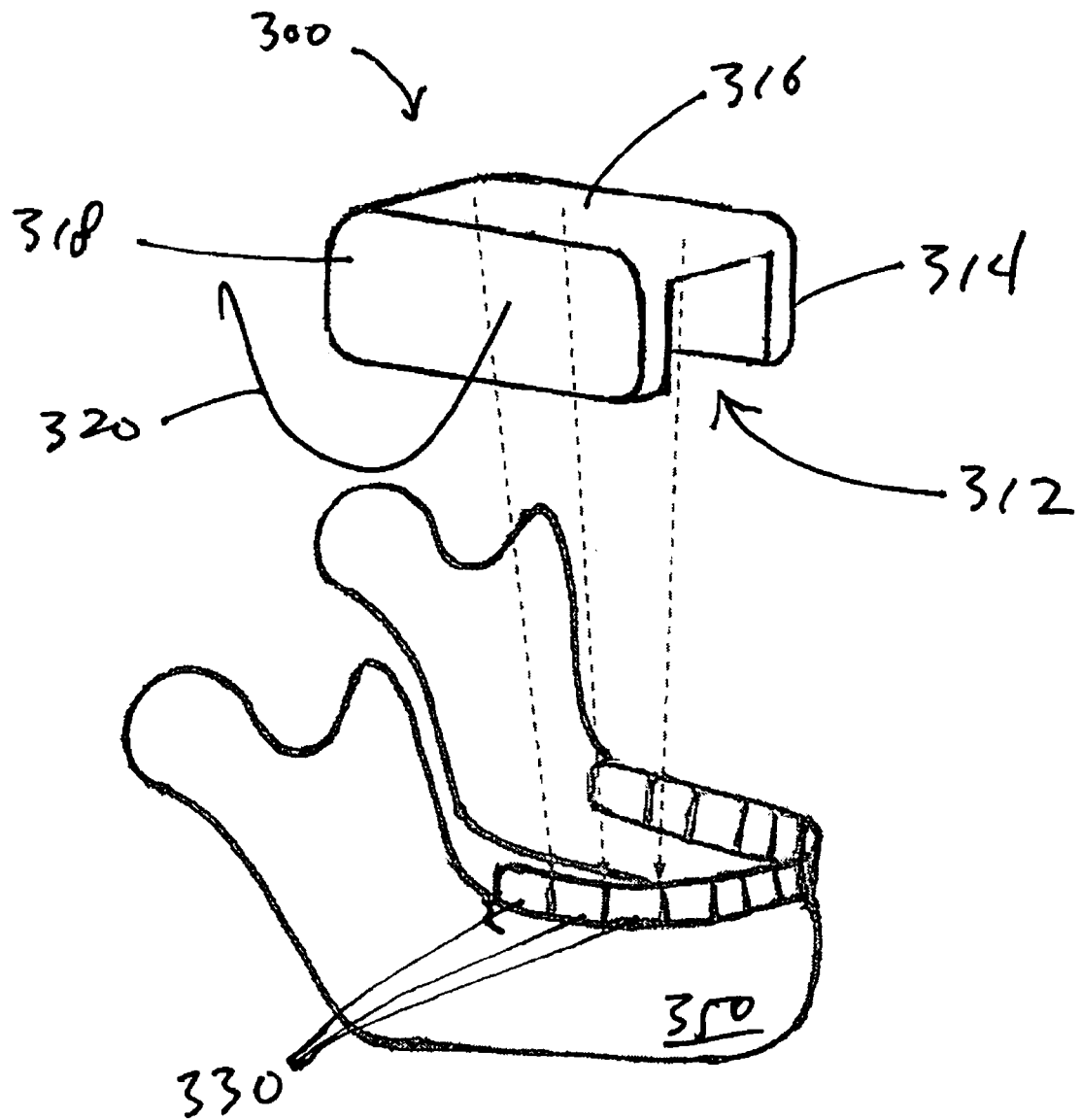
FIG. 3 illustrates in perspective view an embodiment of a temporo-mandibular joint (TMJ) spacer.

FIG. 3 illustrates an embodiment of a right temporo-mandibular joint (TMJ) or dental 300. The illustrated embodiment of the TMJ spacer comprises a body 310 and a flexible cord or leash 320. The body 310 comprises a channel 312 sized and dimensioned to cover the biting surfaces of the user's molars, and optionally, the premolars, collectively 330. In the illustrate embodiment, the covered teeth are of the lower jaw. Those skilled in the art will understand that in some embodiments, the channel 312 covers the teeth of the upper jaw, and/or both jaws. The channel 312 defines an inner wall 314, an upper wall 316, and an outer wall 318. In some embodiments, the thicknesses of the walls 314, 316, and 318 are independently from about 1 mm (0.04") to about 4 mm (0.16"), preferably, about 1.5 mm±0.7 mm (¹⁄₁₆±¹⁄₃₂"). In some preferred embodiments, the walls 314, 316, and 318 have substantially the same thicknesses. The body 310 comprises any suitable material, for example, a polymer. Examples of suitable polymers include polyethylene, polypropylene, and the like. In preferred embodiments, the body 310 is manufactured as a single piece from a single material, thereby reducing manufacturing costs. The cord 320 is secured to the outer wall 318, and prevents swallowing of the TMJ spacer 300. A left TMJ spacer (not illustrated) is also typically used, which is substantially identical to the right TMJ spacer 300, but is disposed on the other side of the user's jaw. In some preferred embodiments, the cords 320 of the left and right TMJ spacers 300 are joined. The TMJ spacers protect the user's teeth and TMJ, as discussed below.

Figure 4:
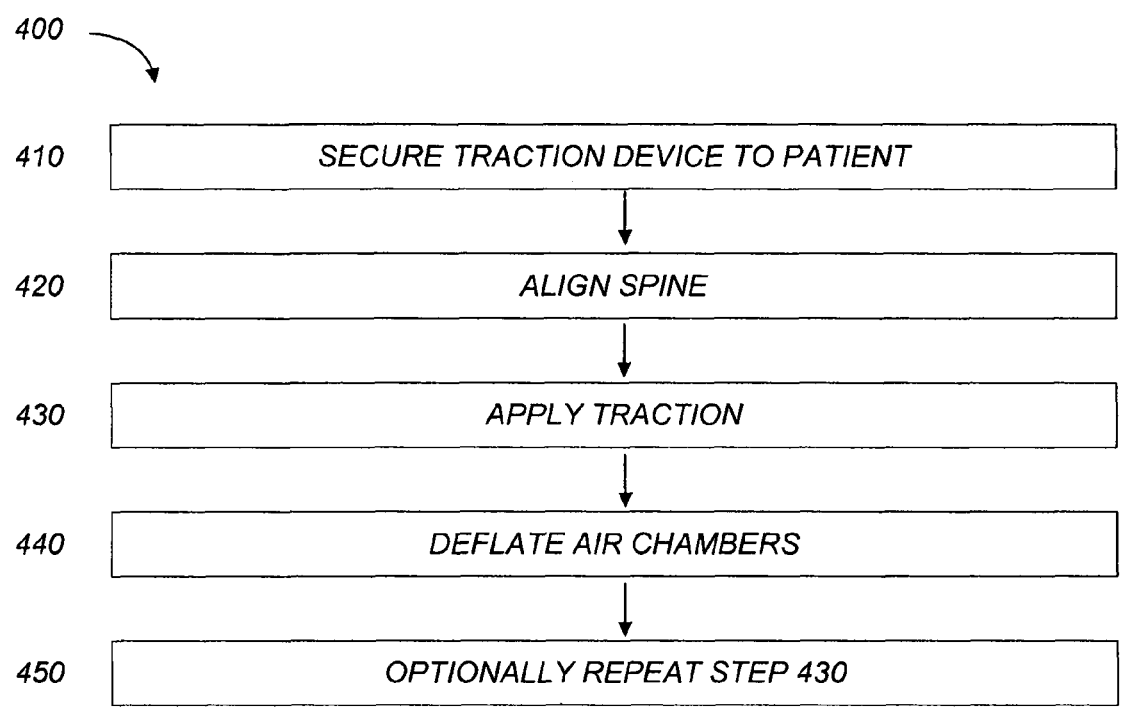
FIG. 4 is a flowchart illustrating a method for using the inflatable four-chamber collar of FIG. 1.
Figure 5A:
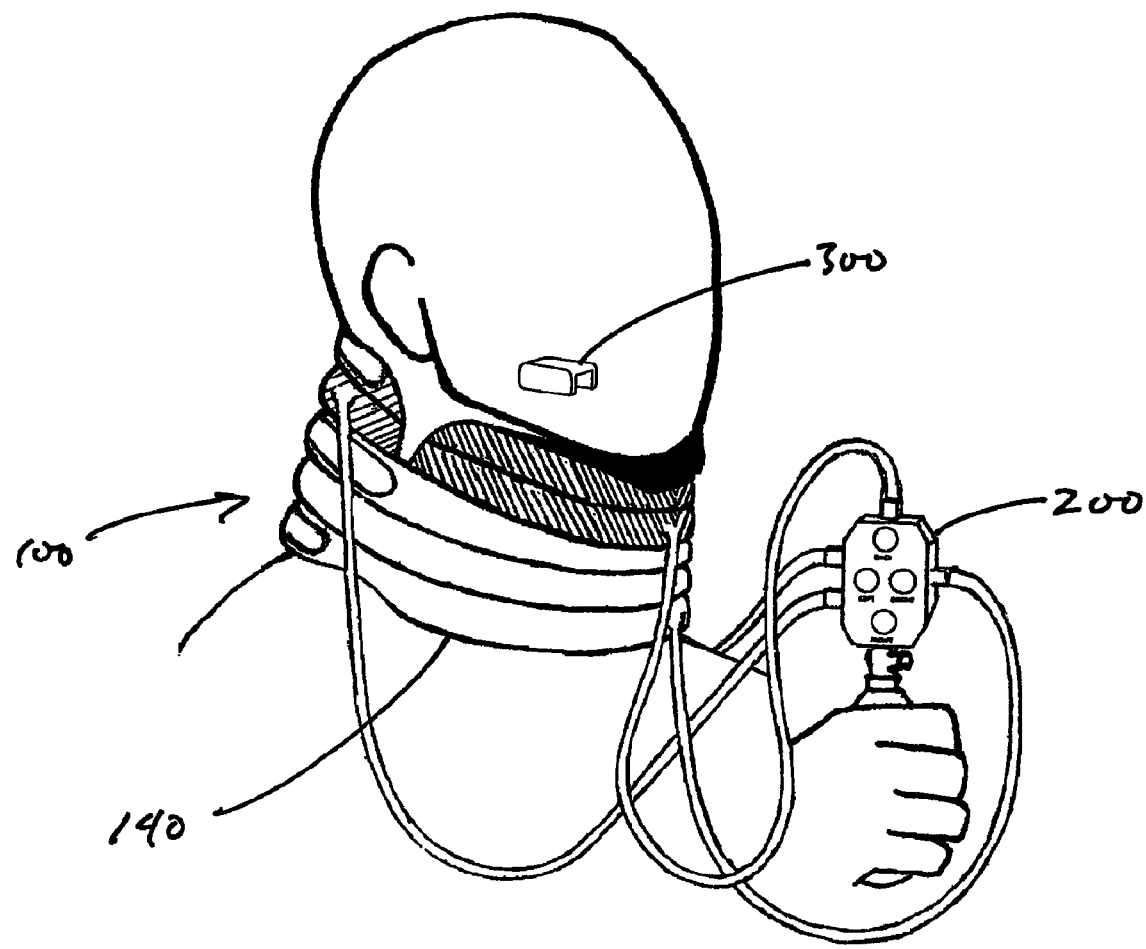
FIG. 5A is a perspective view illustrating schematically a configuration of an embodiment of a traction system comprising the collar of FIG. 1, the manifold of FIG. 2, and the TMJ spacer of FIG. 3.

FIG. 4 is a flowchart illustrating an embodiment of a method 400 for using the collar 100 with reference to FIGS. 1A-1D, 2, 3, 5A, and 5B. In step 410, traction device is positioned on the user. The collar 100 of FIG. 1 is positioned and fastened around a user's neck, as illustrated in FIG. 5A. As discussed above, the collar 100 is fastened with the opening towards the user's back using the provided fastening means. The shoulders are engaged in cutouts 144 provided on the bottom chamber. The manifold 200 and hand bulb of FIG. 2 is connected to the tubing ports of the collar 100 with tubing, as discussed above. Right and left TMJ spacers 300 (only right illustrated) are positioned over the user's molars and are held in place between the upper and lower jaws. In the embodiment illustrated in FIG. 5A, the user's torso is upright, for example, sitting or standing. Any body position is useful in practicing method 400, however. For example, in other embodiments, the user is lying down, reclining, or in another position.

In step 420, the spine is oriented or aligned using the device 100. The bottom chamber 140 is inflated until the chin cup 190 contacts the user's chin (acupuncture: gall bladder 20). The rear chambers 160 and 170 are inflated until the occipital cutouts 164 and 174 of the right and left rear chamber contact the user's occipital regions of the head (acupuncture: conception vessel 23). Inflating the bottom chamber also applies downward pressure on tops of the user's shoulders (upper trapezius muscles; acupuncture: gall bladder 21). The cervical vertebrae are aligned in flexion, extension, and lateral flexion in this step.

Figure 5B:
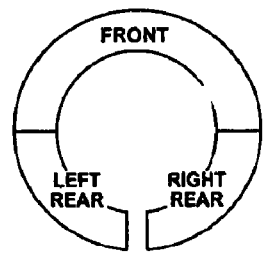
FIG. 5B schematically illustrates a top view of the collar of FIG. 1.

In step 430, traction is applied to the spine. The design of the collar permits simultaneous axial distraction, and one of selective flexion, extension or lateral flexion of the neck using the three air chambers in the top section 106 of the collar. FIG. 5B is a schematic top view of the top section 106 of the collar: the front connector 150, right rear 160, and left rear 170 chambers. Inflating the left rear chamber tilts the neck to the right. Inflating the right rear chamber tilts the neck to the left. Inflating both the left and right rear chambers tilts the neck forward (flexion). Inflating the front chamber tilts the neck back (extension).

Preferred sequences for inflating the air chambers are referred to herein as "spiral traction." As used herein, the term "spiral traction" refers to both sequences comprising steps of cervical traction contemporaneous with neck extension, flexion, or lateral flexion, as well as treatment methods comprising such sequences. The particular use will be clear based on the context. One preferred sequence is referred to as a "figure-eight sequence," and uses the following inflation sequence: left rear, right rear, both rear, front. Another preferred sequence is referred to herein as a "circular sequence," and uses the following inflation sequence: left rear, both rear, right rear, front. Those skilled in the art will understand that some embodiments of the spiral traction sequences have different start and end points, for example, starting with the front chamber, that is the sequence is phase shifted. Those skilled in the art will also understand that the order of the steps in the sequence is reversed in some embodiments, for example, right rear before left rear.

In some preferred embodiments, the inflation rates for the air chambers are controlled to provide a desired therapeutic effect. For example, embodiments of the method provide one or more of spinal traction, mobilization, and/or manipulation. Mobilization typically refers to low-speed methods, while manipulation refers to high-speed methods. Accordingly, embodiments of the disclosed method 400 provide simultaneous spinal mobilization and axial distraction. Embodiments using an automated manifold and a non-user generated source of pressurized gas are particularly useful for controlling inflation rates. Some preferred embodiments use a low traction force, which is possible because of muscles are relaxed during the traction.

Figure 5C:
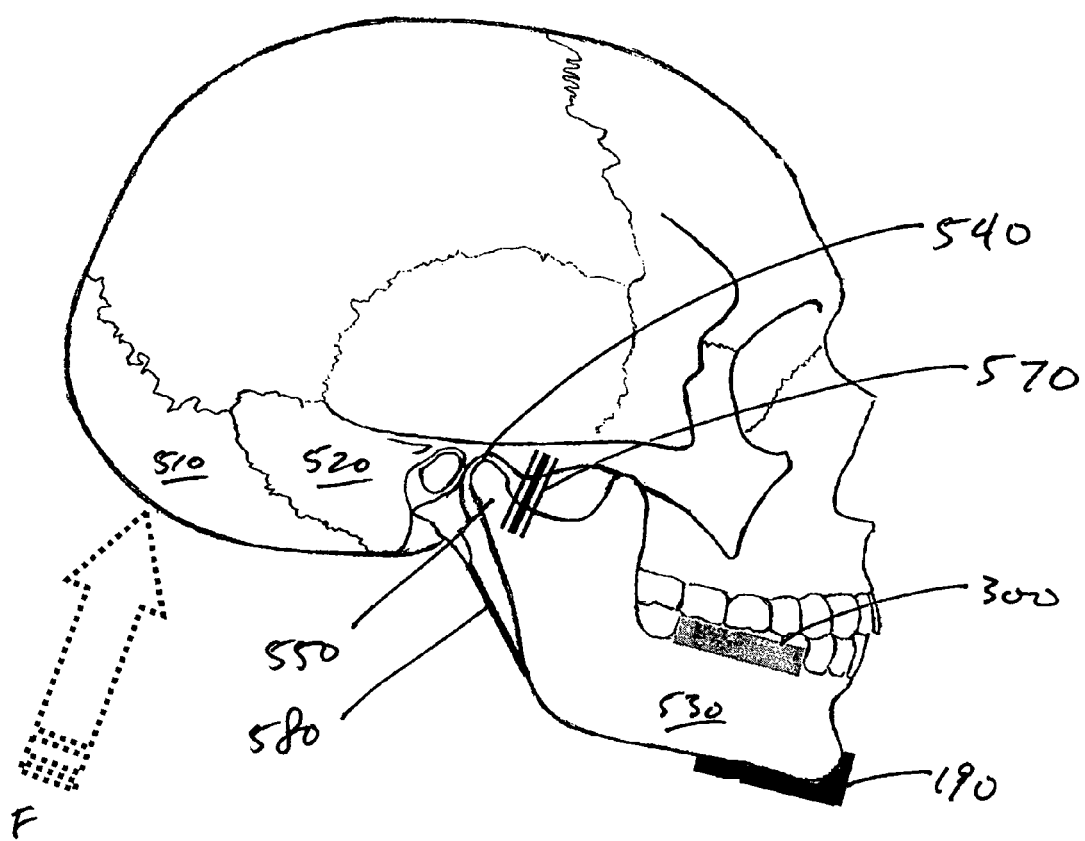
FIGS. 5C and 5D are side views of the skull and TMJ spacer of FIG. 3 illustrating the unloading of the TMJ during the spiral traction procedure.
Figure 5D:
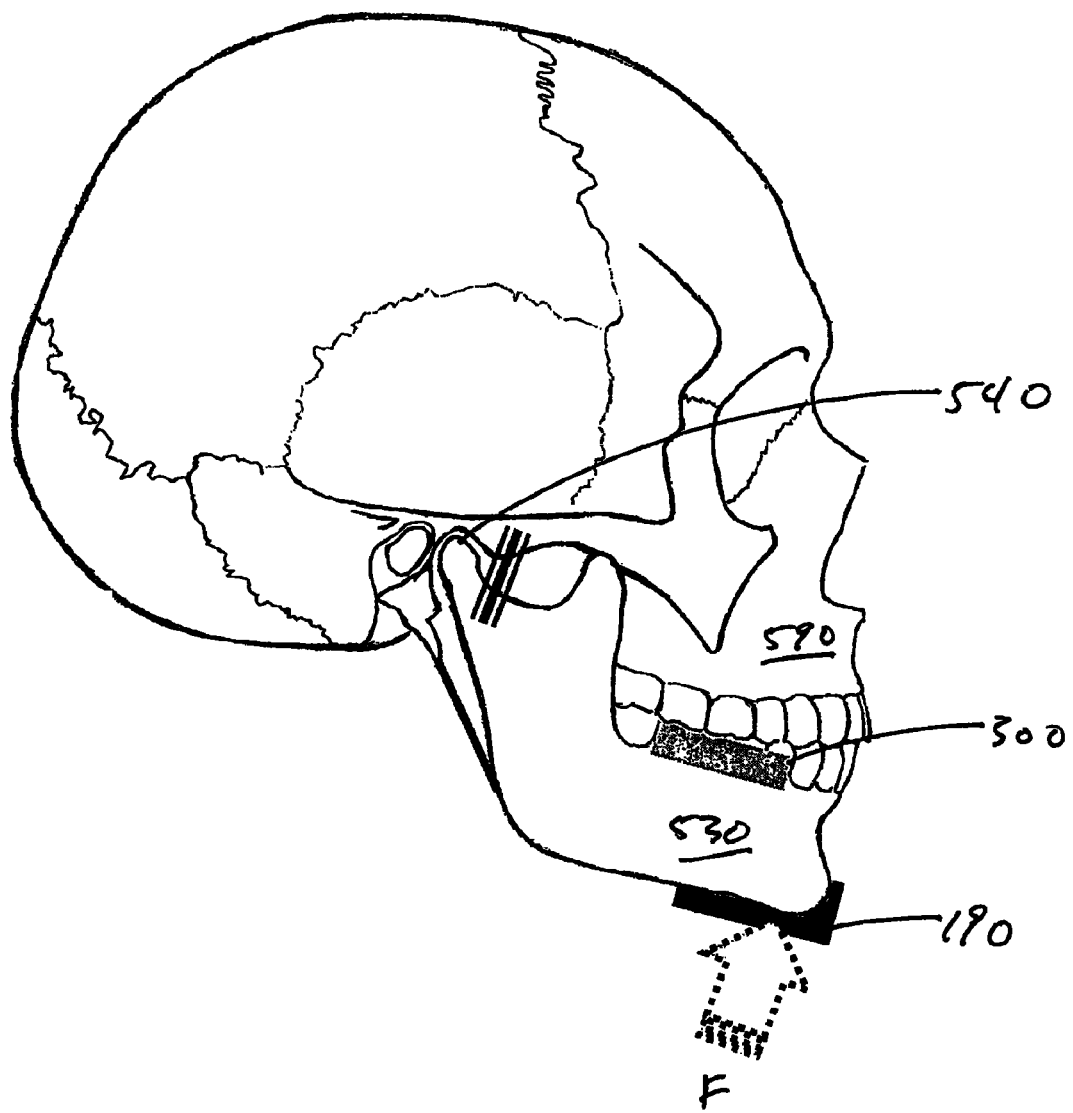

The TMJ spacers 300 unload the temporo-mandibular joint (TMJ) during the spiral traction procedure. FIG. 5C is a side view of the skull illustrating the occipital bone 510, temporal bone 520, and mandible 530. The temporo-mandibular joint (TMJ) 540 is formed between the condylar process 550 of the mandible and the temporal bone 520. The internal and external lateral ligaments 570 and stylo-mandibular ligaments 580 stabilize the TMJ. Also illustrated are the TMJ spacer 300 and the chin cup 190. Inflating one or both of the rear chambers 160 and/or 170 applies a force F to the occipital bone 510, which is transferred through the skull to the chin cup 190. The TMJ spacer 300 acts as the fulcrum of a first-class lever between the TMJ 540 and the chin cup 190, thereby unloading the TMJ 540. FIG. 5D illustrates the situation when the front chamber 150 is inflated, thereby applying a force F directly to the chin cup 190 and unloading the TMJ as discussed above. Embodiments of the TMJ spacer also separate the mandible 530 from the maxilla 590, thereby reducing or eliminating pressure on the front teeth.

It is believed that reactive spasms of the masseter and posterior cervical musculature is avoided by three mechanisms. The lever action of the TMJ spacers 300 unload both TMJs during forward, backward, and side tilting of the neck. Lifting the temporal bones away from the jaw by the rear chambers 160 and 170 unloads both TMJs during forward and backward tilting of the neck, and unloads the ipsilateral TMJ during side tilting. Cushioning by the chin cup and front chamber unloads the contralateral TMJ during side tilting.

Those skilled in the art will understand that the collar 100 is also useful for traditional, axial neck traction by inflating the front and both rear chambers simultaneously.

In step 440, the air chambers are deflated slowly. In some embodiments, the top section 106 (front 150 and rear 160 and 170) chambers are deflated, but the bottom chamber 140 is not, thereby not affecting the alignment provided by the bottom chamber 140. In some embodiments, all of the air chambers are deflated.

In step 450, steps 430 and 440 are optionally repeated. If the bottom chamber 140 was deflated in step 440, step 420 is also repeated. Preferably, the steps are repeated from about 1 to about 9 times, more preferably, about 2 to about 4 times. In some embodiments, one or more different spiral traction sequences are used in the repeated step 440.

Figure 6A:
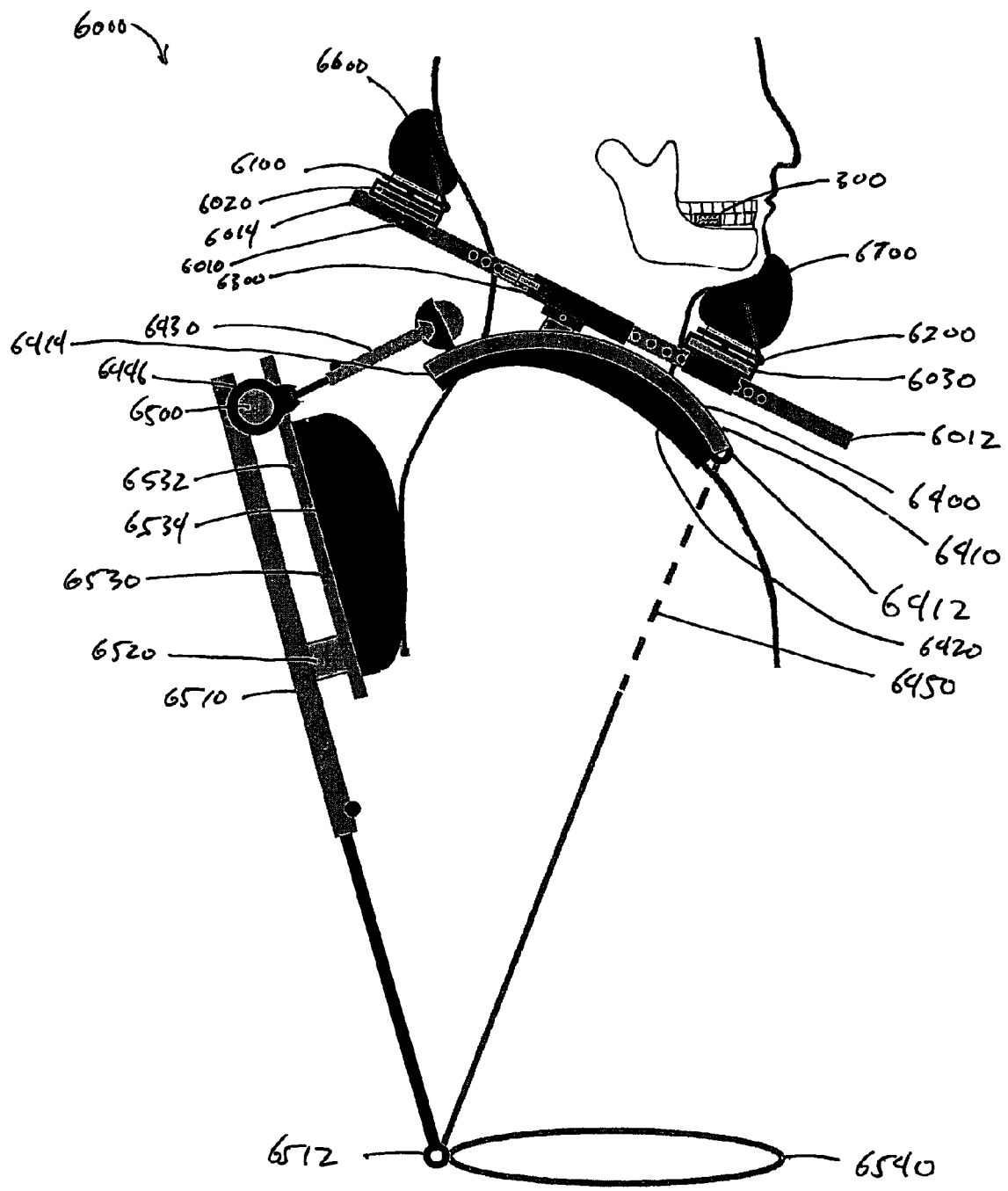
FIGS. 6A, 6B, and 6C are side, back and front views, respectively, of an embodiment of a neck-and-upper-back frame.
Figure 6B:
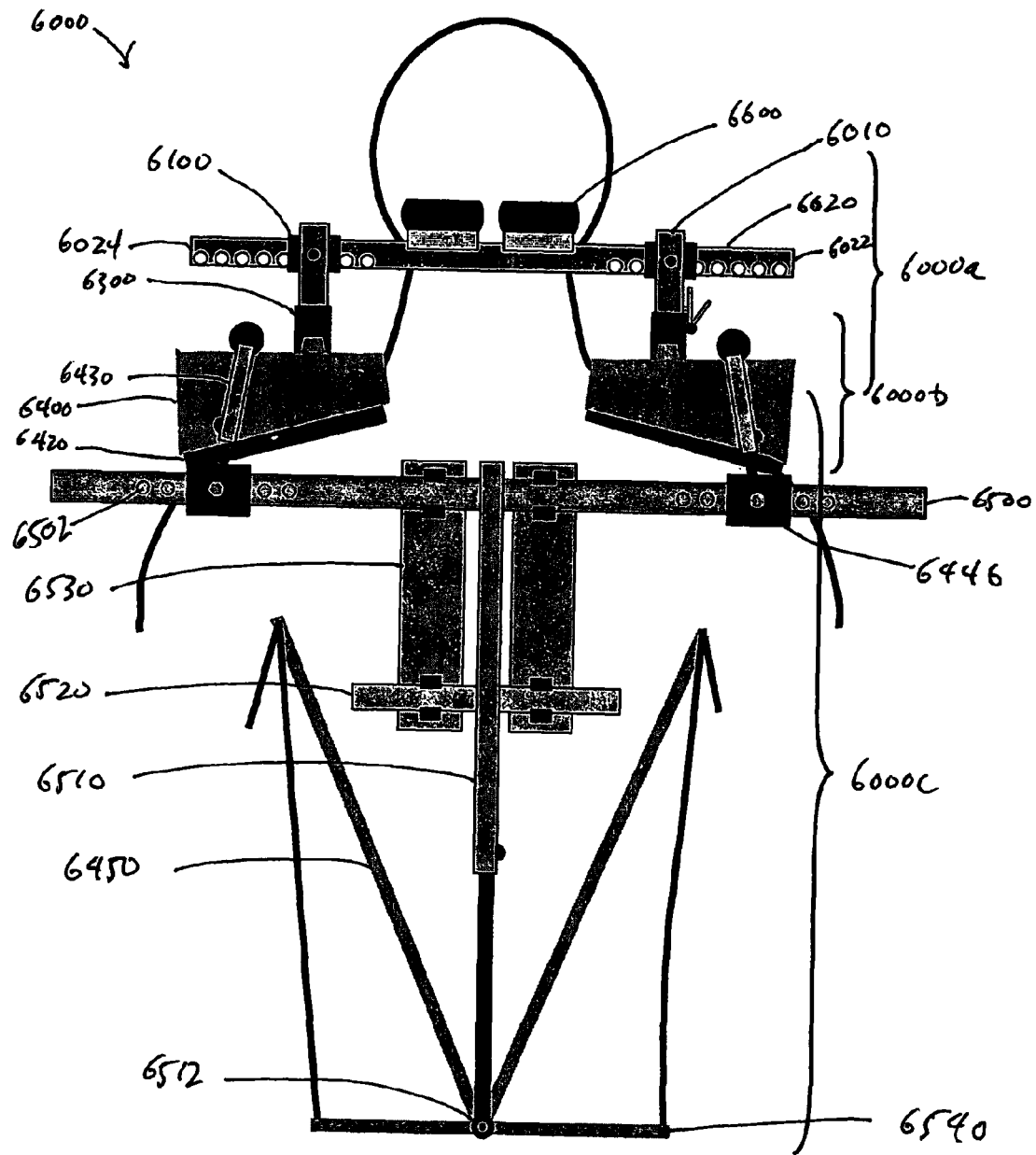
Figure 6C:
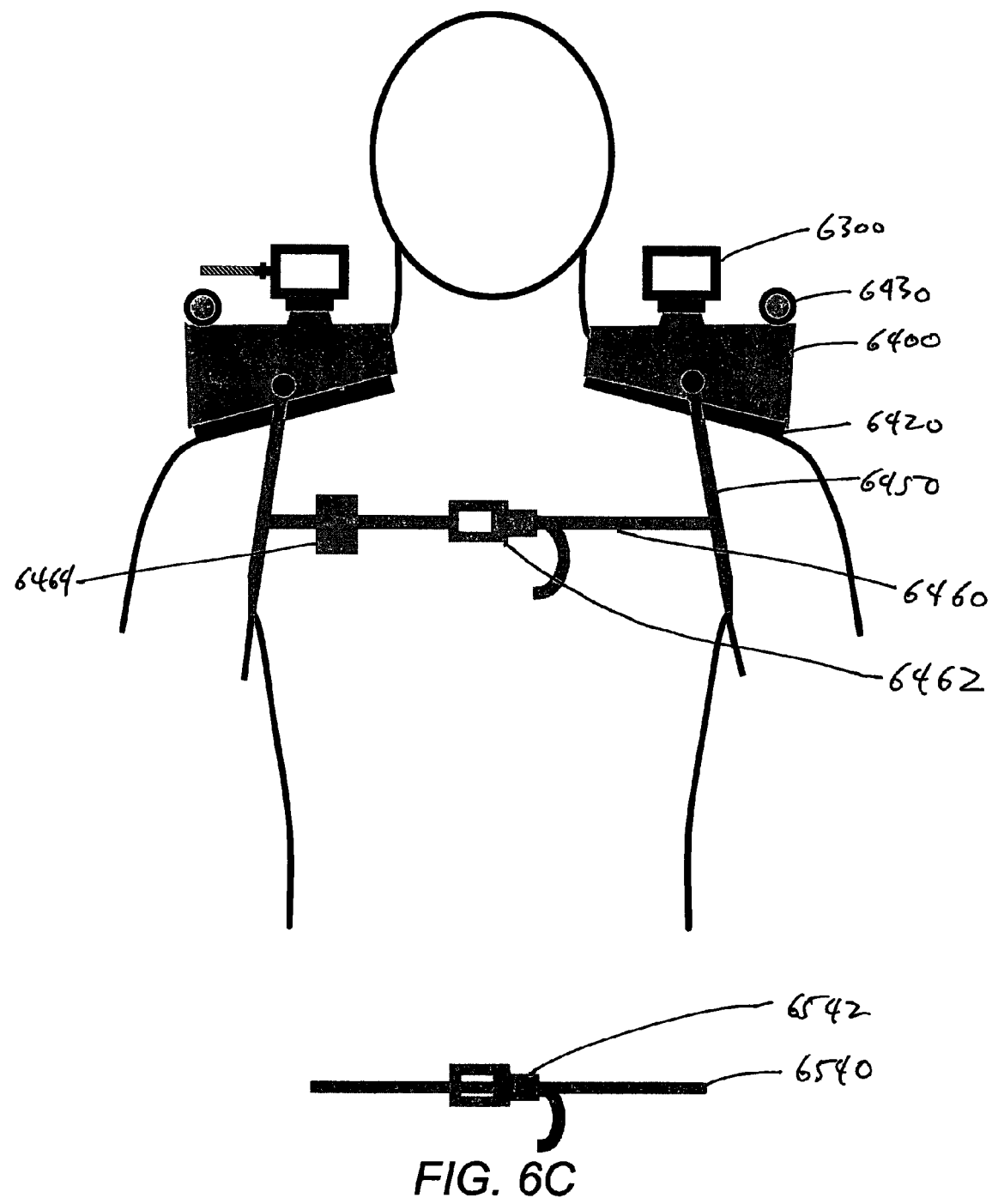

FIGS. 6A-6C are a side view, a back view, and a front view, respectively, of an embodiment of a neck-and-upper-back frame 6000 useful for applying traction to the neck and upper spine. As best seen in FIG. 6B, the device 6000 comprises a neck frame 6000a, a shoulder frame 6000b, and an upper-back frame 6000c. Portions of the neck frame 6000a are not illustrated in the front view 6C.

As best viewed in FIGS. 6A and 6B, the illustrated embodiment of the neck frame 6000a comprises a pair of lateral slats 6010, a rear slat 6020, and a front slat 6030 (not illustrated in FIG. 6B). One lateral slat 6010 is disposed on either side of the user's head. The rear slat 6020 is slidably secured to both lateral slats 6010, and is disposed behind the user's head. The front slat 6030 is slidably secured to the lateral slats 6010, and is disposed in front of the user's neck, below the chin. In a schematic top view illustrated in FIG. 6D, collectively, the right lateral slat 6010a, left lateral slat 6010b, rear slat 6020, and front slat 6030 form a rectangle. Each lateral slat 6010 comprises a first or front end 6012 and a second or back end 6014. The front end 6012 of each lateral slat is positioned in front of the user's head, and the back end 6014 is positioned behind the user's head. The rear slat 6020 comprises a first or right end 6022 and a second or left end 6024. The front slat 6030 also comprises a first or right end 6032 and a second or left end 6034. The right ends of the rear 6022 and front 6032 slats are positioned to the right of the user's head, while the left ends of the rear 6024 and front 6034 slats are positioned to the left of the user's head.

As used herein, the term "slat" refers to elongate substantially rigid structures of any suitable cross-section, and includes structures such as slats, rods, beams, tubes, rails and other structures known in the art. In some embodiments, the slats have a substantially constant cross section along the length. In other embodiment, the cross section of the slat is not constant. Slats comprise any suitable material known in the art, for example, wood, wood composites, metals, polymers, inorganic materials, and combinations thereof. In some embodiments, the slats comprise a composite, for example, a fiberglass composite, a wood composite, and/or a carbon fiber composite.

Returning to FIG. 6A, the rear slat 6020 is mounted to the lateral slats 6010 using a pair of rear slat sleeves 6100. In the illustrated embodiment, each rear slat sleeve 6100 is substantially immovably secured to a corresponding lateral slat 6010. Each rear slat sleeve 6100 permits relative lockably slidable left-right motion between the rear slat 6020 and the corresponding lateral slat 6010. In the illustrated embodiment, the rear slat sleeves 6100 maintain a substantially perpendicular relationship between the rear slat 6020 and each lateral slat 6010. Details of the construction of the rear slat sleeves 6100 are provided below.

The front slat 6030 is mounted to the lateral slats 6010 using a pair of rear slat sleeves 6200. In the illustrated embodiment, each front slat sleeve 6200 is lockably slidably mounted to a corresponding lateral slat 6010, thereby permitting front-back motion of the front slat sleeve 6200 along the corresponding lateral slat 6010. Each front slat sleeve 6200 permits relative lockably slidable left-right motion between the front slat 6030 and the corresponding lateral slat 6010. In the illustrated embodiment, the front slat sleeves 6200 maintain a substantially perpendicular relationship between the front slat 6030 and each lateral slat 6010. Details of the construction of the front slat sleeves 6200 are provided below.

Figure 6D:
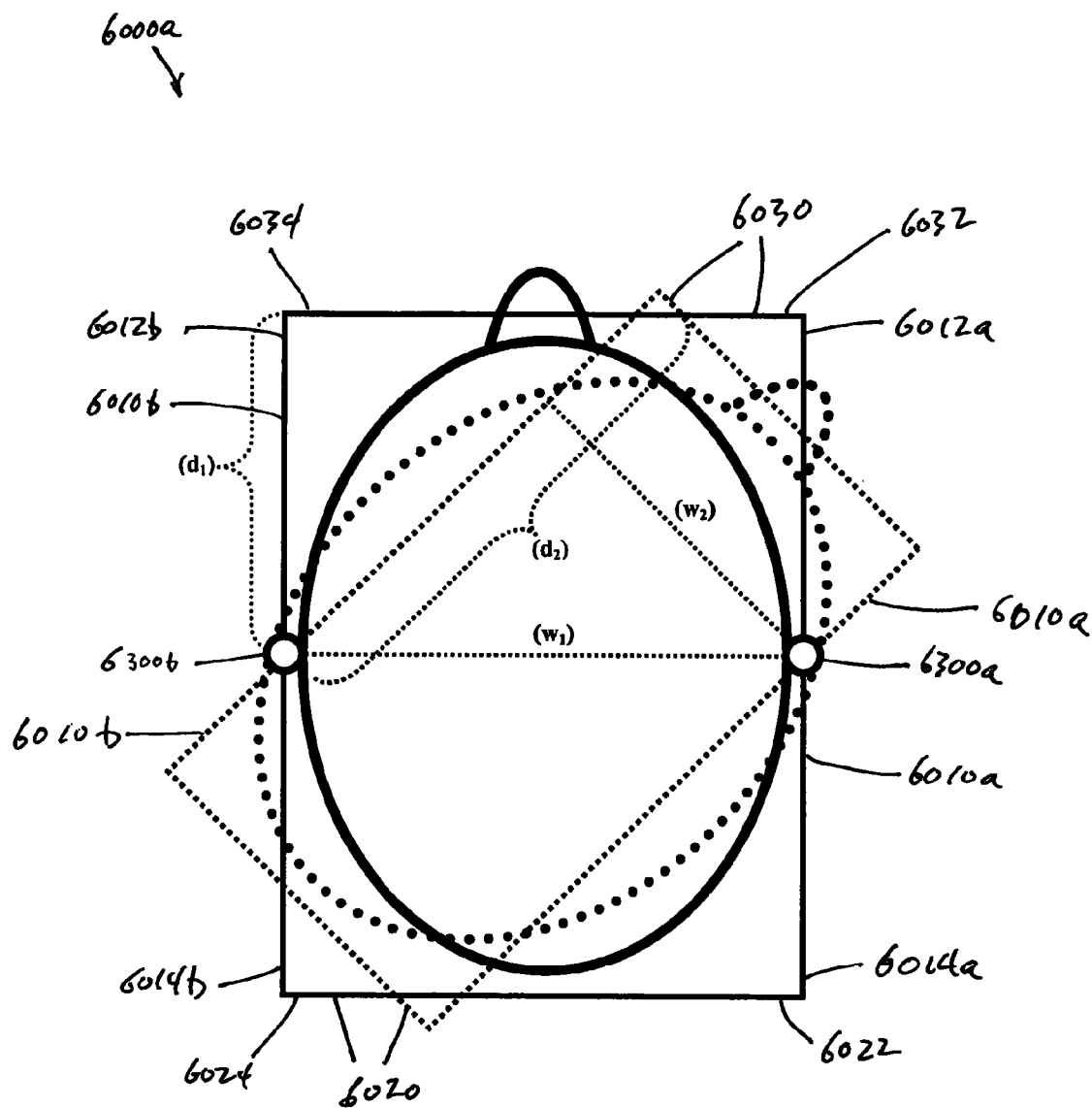
FIG. 6D is a schematic top view of an embodiment of a neck frame.
Figure 6E:
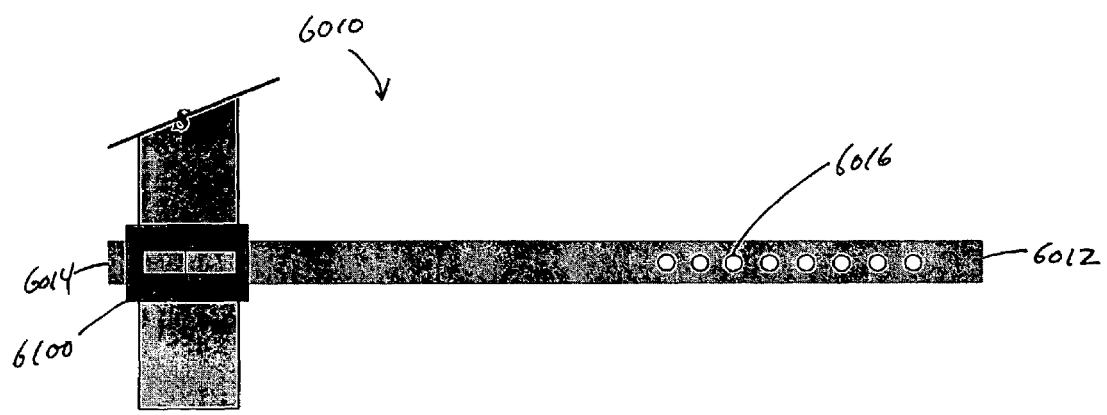
FIGS. 6E and 6F are top and side views, respectively, of an embodiment of a lateral slat.
Figure 6F:
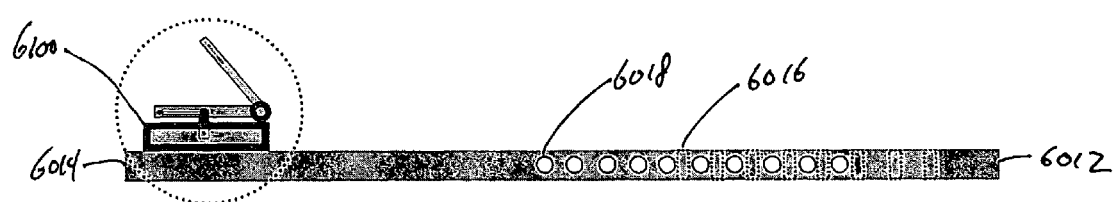

FIGS. 6E and 6F illustrate top and side views respectively of an embodiment of the lateral slats 6010. Each lateral slat comprises a first or front end 6012 and a second or back end 6014. Secured towards the back end 6014 is a rear slat sleeve 6100. As illustrated in FIG. 6E, the rear slat 6020 is substantially perpendicular to the lateral slat 6010 in the rear slat sleeve 6100. A series of openings or holes 6016 extend from the first end 6012 towards the second end 6014. These openings 6016 comprise a component in the locking mechanism of an embodiment of the front slat sleeve 6200 as described below. In the illustrated embodiment, the openings 6016 extend through the lateral slat 6010 from the top to bottom. As shown in FIG. 6F, a second series of longitudinally extending holes or openings 6018 are provided on the sides of the lateral slat 6010. The openings 6018 comprise a component in an embodiment of a mechanism for locking the lateral slat 6010 in the lateral slat sleeve 6100. The openings 6018 are also useful in an embodiment of a front slat sleeve illustrated in FIG. 6M and described below. Some embodiments of the lateral slats 6010 below do not comprise openings 6016 and/or 6018, as discussed.

In the embodiment illustrated in FIGS. 6A and 6B, the rear slat 6020 and front slat 6030 are positioned above the lateral slats 6010 as viewed from the side. Those skilled in the art will understand that other arrangements are possible, for example, with both rear 6020 and front 6030 to slats positioned below the lateral slats 6010, or one of the rear 6020 or front 6030 slats above the lateral slats 6010, and the other below. In some embodiments, at least one of the rear 6020 or front 6030 slats is substantially at the same level as the lateral slats 6010, that is, not above or below the lateral slats 6010. Those skilled in the art will understand that other arrangements are possible. As on the illustrated embodiment, a rear slat sleeve 6100 is not adjustable relative to the lateral slat 6010. Those skilled in the art will understand that in other embodiments, the rear slat sleeve 6100 is adjustable relative to the lateral slat 6010, for example, forward and backward. Those skilled in the art will also understand that, in some embodiments, the front slat sleeve 6200 is not adjustable forward and backward relative to the lateral slat 6010.

The illustrated embodiment of the neck frame 6000a also comprises a right occipital cup 6600a and a left occipital cup 6600b (generally, 6600). The right occipital cup 6600a is sized and dimensioned to engage the user's right left occipital region of the head. Similarly, the left occipital cup 6600b is sized and dimensioned to engage the user's left occipital region of the head.

The occipital cups 6600 are removably mounted to the top of the rear slat 6010 and are spaced to engage a user's occipital regions of the head. The occipital cup 6600 air chambers are slightly larger than the occipital regions of the head in some embodiments. In some embodiments, at least one of the occipital cups 6600 is longitudinally adjustable along the rear slat 6010, thereby providing an adjustable distance between the two occipital cups 6600.

Also provided is a chin cup 6700 sized and dimensioned to engage a user's chin. In the illustrated embodiment, the chin cup 6700 is removably mounted to the top of and substantially at the center of the front slat 6030. Each of the occipital cups 6600 and the chin cup 6700 comprises one or more inflatable air chambers, which are configured for independent, user controlled inflation, as discussed in greater detail below.

The air chambers in the occipital cups 6600 are referred to herein as "rear chambers." The air chamber in the chin cup 6700 is referred to herein as a "front chamber." The air chambers comprise a flexible, substantially airtight material. In some embodiments, the air chambers comprise an elastic material. Examples of suitable materials for the air chamber are known in the art, and include polymers, natural rubber, synthetic rubber, and the like. In some embodiments, the air chamber comprises fibers and/or a fabric embedded in and/or covered with a substantially airtight material. Each of the air chambers comprises one or more inflation ports through which a gas is introduced and/or removed. One or more tubes fluidly connect the inflation ports to a source of pressurized gas, preferably through a manifold, as discussed below.

In some embodiments, at least one of the occipital cups 6600 and/or chin cup 6700 comprises a rigid and/or semi-rigid shell and/or platform to which the respective air chamber is secured. In some embodiments, the shell and/or platform is used to secure the occipital cup 6600 and/or chin cup 6700 to the rear 6020 and/or front 6030 slat, respectively. In some embodiments, the shell and/or platform shields and/or protects the air chamber, for example, by covering at least a portion of the air chamber. In some embodiments, a shell and/or platform is shaped to direct the force generated by the inflation of the air chambers. In some embodiments, the shell and/or platform comprised a lightweight and formable material, for example, a polymer, a metal, wood, a wood composite, or the like. In some embodiments, the material is a reinforced composite, for example, a fiber reinforced polymer, fiberglass, or the like. In some embodiments, one or more of the air chambers is replaceable, for example, for providing a range of size, and/or for repair. In some embodiments, one or more of the air chambers is substantially permanently mounted to the shell and/or platform.

Figure 6G:
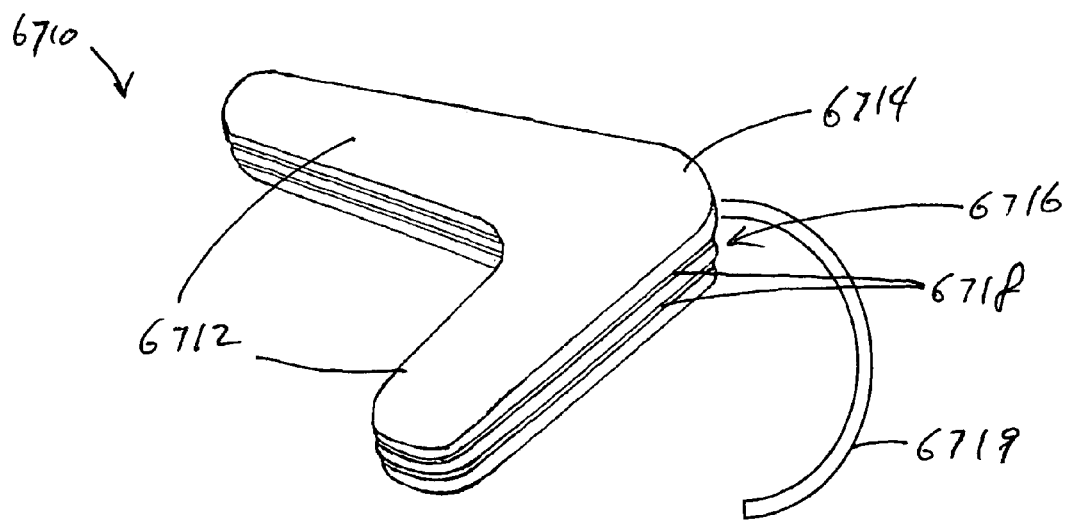
FIG. 6G is a perspective view of an embodiment of a front chamber.

FIG. 6G is a perspective view of an embodiment of a front air chamber or front chamber 6710 which is mounted in the chin cup 6700. The front chamber 6710 is generally boomerang-shaped, with a pair of arms 6712 converging at an angle to form a point 6714. The sides 6716 of the air chamber comprise a plurality of corrugations 6718, which permit the front chamber 6710 to expand and contract vertically on inflation and deflation. A tube 6719 in fluid connection with the interior of the front chamber 6710 permits inflation and deflation of the front chamber. In the illustrated embodiment, the front chamber 6710 extends about half the distance from the front of the chin to the angle of the mandible. In some embodiments, the front chamber 6710 is provided in a variety of sizes to fit different users, for example, small, medium, and large sizes for adults. Some embodiments provide one or more front chambers 6710 in children's sizes.

As discussed above, some of the mechanisms in the device 6000, for example, the rear slat sleeve 6100, the front slat sleeve 6200, and the lateral slat sleeve 6300 provide releasable locking of a slat therein. Those skilled in the art will understand that any suitable locking means known in the art is useful. For example, in some embodiments disclosed herein, an opening or a hole is provided in a slat, and a plunger or pin on a slat sleeve engages the opening in the slat. The plunger is lockable using, for example, a lever. Those skilled in the art will understand that the opening or hole is a through hole in some embodiments, and a blind hole in some embodiments. This mechanism is used, for example, in embodiments of the rear slat sleeve 6100, front slat sleeve 6200, and other mechanisms described herein. Those skilled in the art will understand that other locking mechanisms known in the art are used in other embodiments. For example, in some embodiments, the locking mechanism comprises a clutch in which two adjacent pressure plates against each other are forced against each other, for example, a portion of a slat sleeve and a portion of a slat. In some embodiments, at least one of the pressure plates comprises a textured surface and/or a high friction surface. Those skilled in the art will understand that holes or openings in the slats described herein are optional in embodiments comprising a clutch.

Some embodiments described herein use a locking device known in the art referred to herein as a "push button," which comprises a first component comprising a spring loaded button or pin biased outward, and a second component comprising at least one opening or hole sized and dimensioned to engage the pin. The mechanism is unlocked by depressing the pin clear of the second component and moving the second component relative to the first component. The mechanism is locked by moving an opening of the second component over the pin, which is biased outward, thereby engaging the opening. In some embodiments, operation of the mechanism is facilitated by rounding the top of the pin and/or chamfering the opening.

Other suitable locking means known in the art are also useful, for example, screws, detents, clips, clasps, latches, pins, pawls, notches, combinations, and the like. In some embodiments, the locking mechanism is automated, for example, using a motor, a pneumatic device, a piezoelectric device, an electromechanical device, a magnetic device, combinations thereof, and other devices known in the art.

Figure 6H:
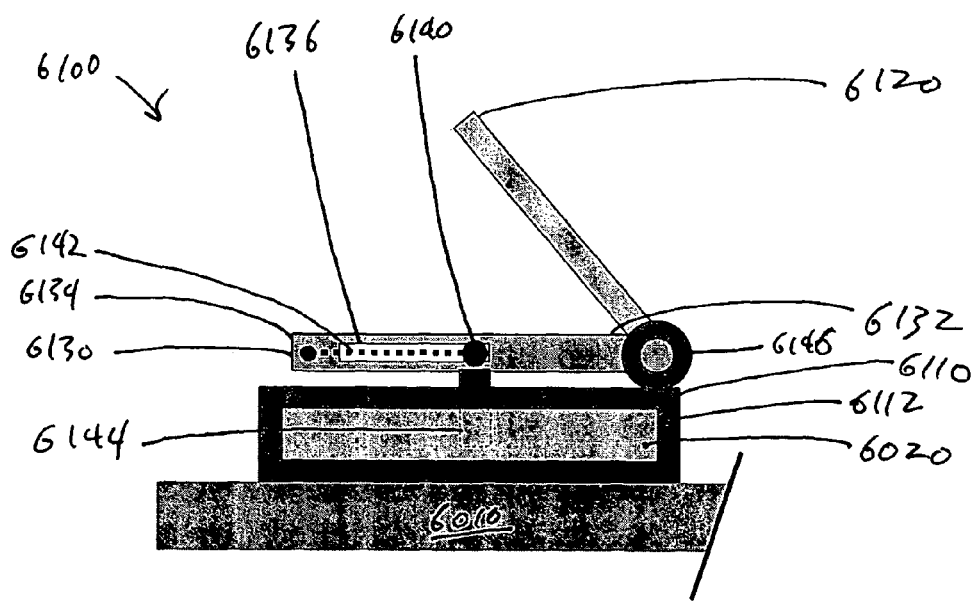
FIGS. 6H, 6I, and 6J are a side view in the locked position, a side view of in the unlocked position, and a rear view in the locked position, respectively, of an embodiment of a rear slat sleeve.
Figure 6I:
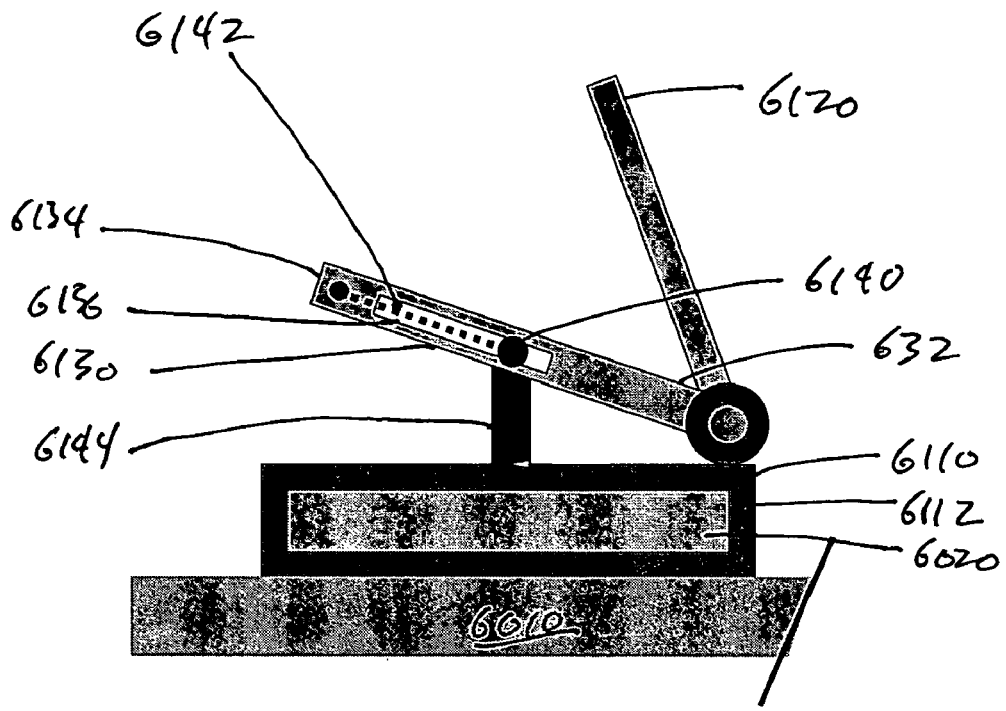
Figure 6J:
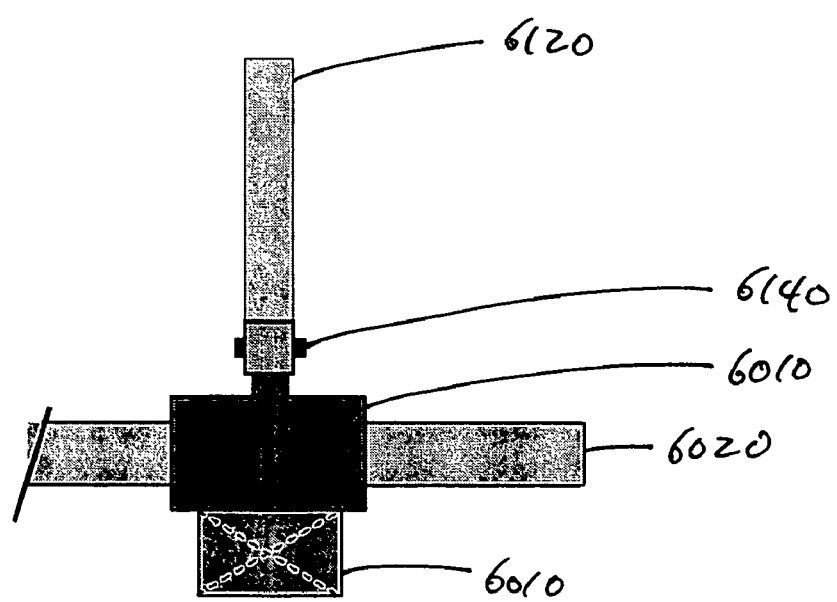

FIGS. 6H and 6I illustrate side views, and FIG. 6J illustrates a rear view of an embodiment of a rear slat sleeve 6100. As discussed above, in some embodiments, the rear slat sleeve is fixedly secured to a lateral slat 6010. The rear slat sleeves 6100 are configured to maintain the lateral slats substantially perpendicular to the rear slat 6010. Accordingly, in some embodiments, the rear slat sleeve 6100 substantially inhibits rotation between the lateral slat 6010 and the rear slat 6020. The illustrated embodiment of the rear slat sleeve 6100 comprises a body 6110, through which is formed a channel 6112 sized and dimensioned to slidably receive the rear slat 6020. The body 6110 is mounted on a lateral slat 6010. An upper lever arm 6120 secured to a lower lever arm 6130 are pivotably mounted as a single unit near an edge of the body 6110 using a hinge 6148. A slot 6136 extends from near the second end 6134 towards the first end 6132 of the lower lever arm. In the illustrated embodiment, the slot 6136 extends through the sides of and opens to the bottom of the lower lever arm 6130, resulting in a generally T-shaped cross section. A pin 6140 is slidably disposed across, the crossbar of the T-shaped slot 6136, as best viewed in FIG. 7J. A spring 6142 under tension extends between the pin 6142 and the second end 6134 of the lower lever arm. Pivotably attached to the pin 6140 is a plunger 6144, which is sized and dimensioned to engage any one of a series of openings or holes 6026 in the rear slat (FIG. 6B).

FIG. 6I illustrates the rear slat sleeve 6100 in the unlocked position. Lifting the upper lever arm 6120 also lifts the lower lever arm 6130, thereby lifting the plunger 6144 from the opening 6026 in the rear slat. As the lower lever arm 6130 is lifted, the spring 6142 pulls the pin 6140 towards the second end 6134 of the lower lever arm, thereby maintaining the plunger 6144 substantially normal to the rear slat 6020 and body 6110 and preventing binding. FIG. 6J is a rear view of the rear slat sleeve 6100 in the locked position. Those skilled in the art will understand that the upper lever arm 6120 is optional in some emobdiments.

Figure 6K:
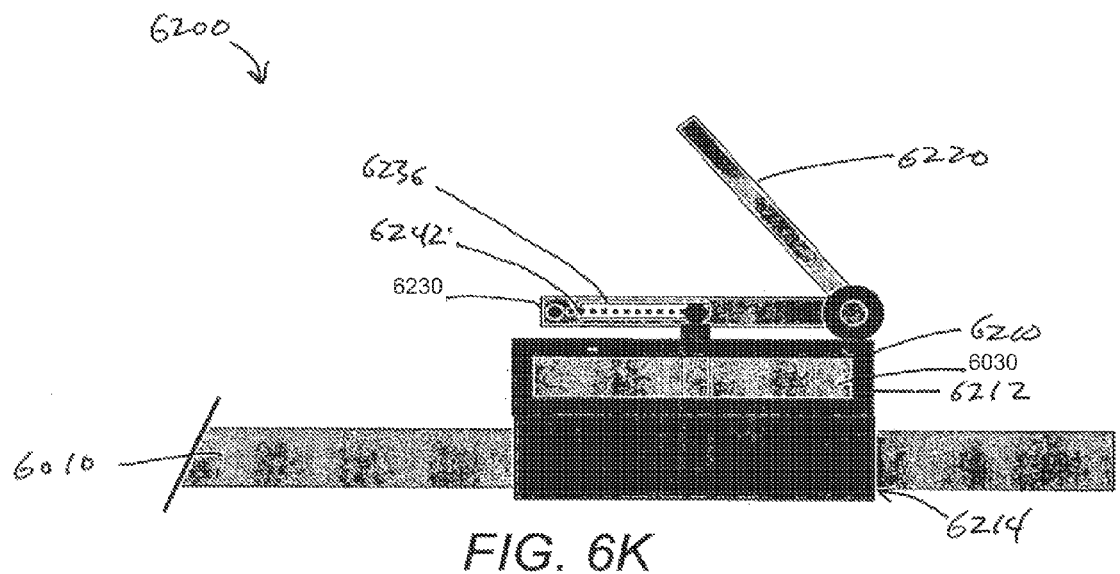
FIGS. 6K and 6L are a side view and a rear view in the locked position, respectively, of an embodiment of a front slat sleeve.
Figure 6L:
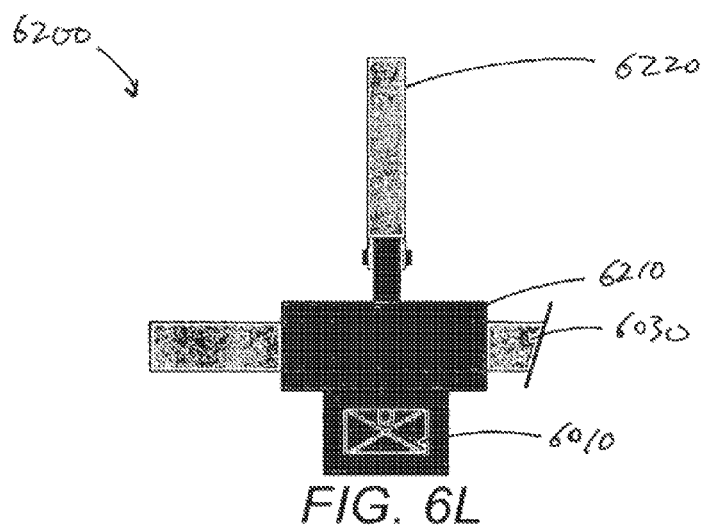

FIGS. 6K and 6L illustrate an embodiment of a front slat sleeve 6200 that is substantially similar to the rear slat sleeve 6100 illustrated in FIGS. 6H-6J and described above. In the illustrated embodiment, the front slat sleeve 6200 comprises a body 6210 and a first channel 6212 formed therethrough, which sized and dimensioned to slidably receive a front slat 6030. The body 6210 also comprises a second channel 6214 sized and dimensioned to slidably receive a lateral slat 6010. The relative orientation of the first channel 6212 and the second channel 6214 constrains a perpendicular relationship between the front slat 6030 and the lateral slat 6010. The configuration of the upper lever arm 6220, lower lever arm 6230, spring 6242, slot 6236, pin 6240, and plunger 6244 are substantially as described above for the rear slat sleeve 6100. In the illustrated embodiment, the plunger 6244 simultaneously engages an opening in the front slat 6030 and an opening 6016 in the lateral slat (FIG. 6E).

Figure 6M:
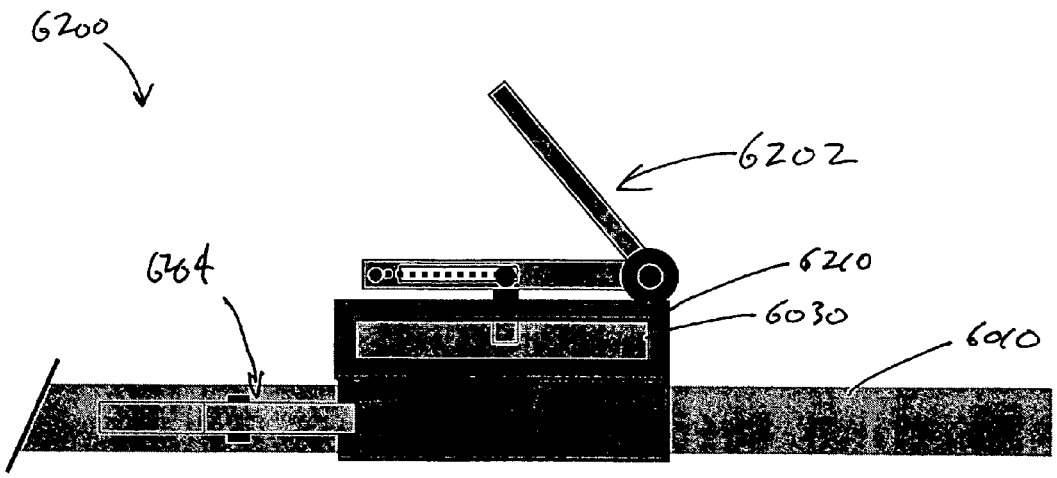
FIG. 6M is a side view of another embodiment of a front slat sleeve.

FIG. 6M illustrates an embodiment of a front slat sleeve 6200, where the front slat 6030 and lateral slat 6010 are each provided with separate locking mechanisms, each of which is substantially similar to the locking mechanisms described above for the rear slat sleeve 6100. A first locking mechanism 6202 engages an opening in the front slat 6030. A second locking mechanism 6204 engages an opening 6018 in the lateral slat 6010 (FIG. 6F).

Returning to FIGS. 6A-6C, the shoulder frame 6000b comprises a pair of lateral slat sleeves 6300 mounted to corresponding shoulder pads 6400. The lateral slats 6010 are mounted to the lateral slat sleeves 6300, thereby operatively joining the neck frame 6000a to the shoulder frame 6000b. Each shoulder pad 6400 comprises a body 6410 comprising a relatively rigid, strong, and lightweight material, known in the art for example, wood composites, polymer composite, fiberglass, metal, or the like. In the illustrated embodiment, the body 6410 is sized and dimensioned to conform to a shoulder. The body comprises a front end 6412 and a back end 6414. To the underside of the body 6410 is secured an inflatable shoulder chamber 6420. The shoulder chamber 6420 has an arched shape sized and dimensioned to conform to a user's shoulder, and in the illustrated embodiment, extends from the sternum to the acromion process of the scapula, and from the second or third anterior intercostal space to the top of the scapula. Suitable materials for the shoulder chamber 6420 are discussed above and below.

To the back end 6414 each shoulder pad is mounted a rear bracket 6430 extending backwards. Details of the rear bracket are provided in greater detail below. A shoulder strap 6450 mounted to the front end 6412 of the shoulder pad, for example, to an eyelet. A chest strap 6460 extends across a user's chest between the shoulder straps 6450. In the illustrated embodiment, the chest strap 6460 comprises an adjustable clasp or buckle 6462. In the illustrated embodiment, the chest strap 6460 further comprises a clip 6464 for mounting the control manifold, which is discussed in greater detail below.

Figure 6N:
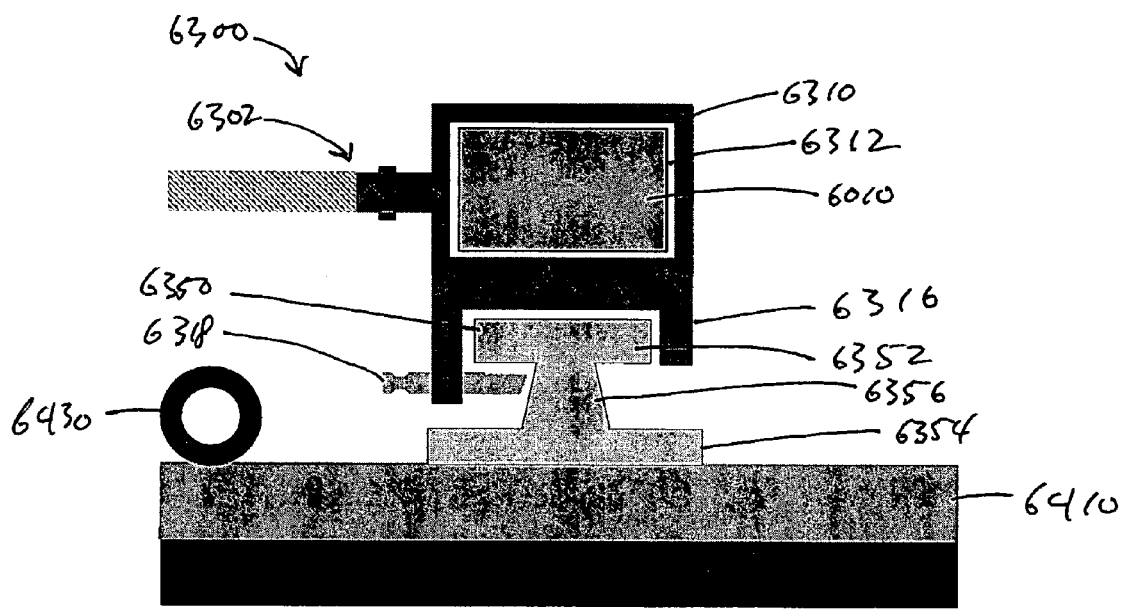
FIG. 6N is a front view of an embodiment of a lateral slat sleeve.

FIG. 6N illustrates a front view of an embodiment of a lateral slat sleeve 6300. In the illustrated embodiment, the lateral slat sleeve 6300 comprises a body 1110, through which a channel 6312 is formed. The channel 6312 is sized and dimensioned to slidably receive a lateral slat 6010 therethrough. A lever-and-plunger-type locking mechanism 6302 of the type described above is provided on the body 6310. The locking mechanism 6302 releasably engages an opening 6018 in the lateral slat (FIG. 6F), thereby controlling the sliding of the lateral slat 6010 in the channel 6312. A bushing 6316 is formed on the lower portion of the body 1110. The bushing 6316 is sized and dimensioned to accept and rotate on an enlarged head 6352 of a tilting lever 6350. In the illustrated embodiment, the head 6352 is substantially cylindrical. The head 6352 is formed on tilting lever 6350, which also comprises a tape 6354 and a shank 6356 extending between the tape 6354 and head 6352. The shank 6356 has a smaller diameter than the head 6352. Also provided are a one or more retaining pins 6358 which retain the bushing 6316 on the head 6352 of the tilting lever. In some embodiments, the retaining pin or pins 6358 are removable to permit disassembly. In the illustrated embodiment, the base 6354 of the tilting lever is substantially fixedly secured to the top of the shoulder pad body 6410, and oriented to provide a forward tilt to the neck frame 6000*a*, as illustrated in FIG. 6A.

Figure 6O:
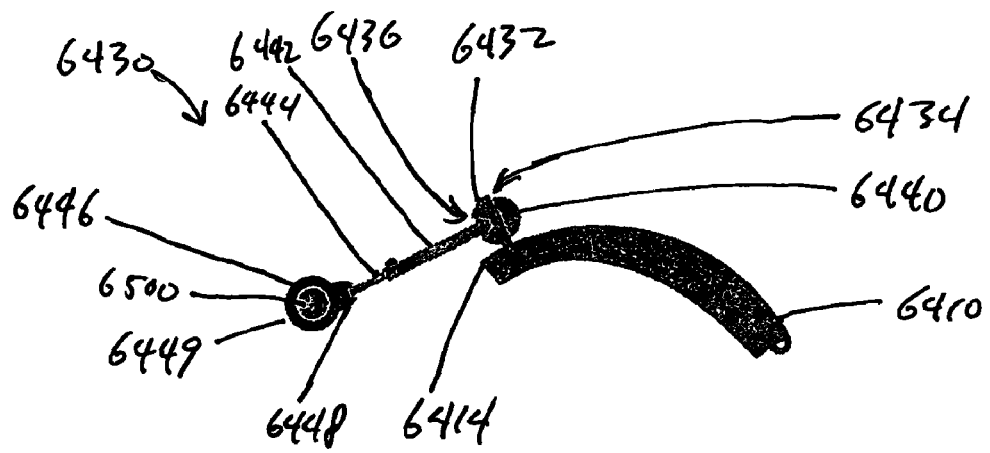
FIGS. 6O, 6P, and 6Q are side views of three embodiments of a rear bracket.
Figure 6P:
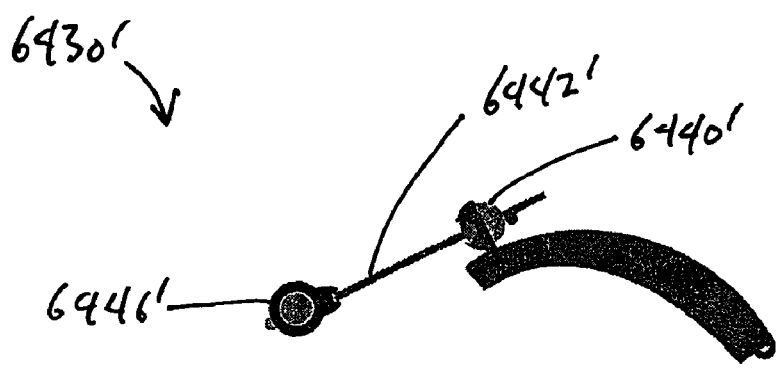
Figure 6Q:
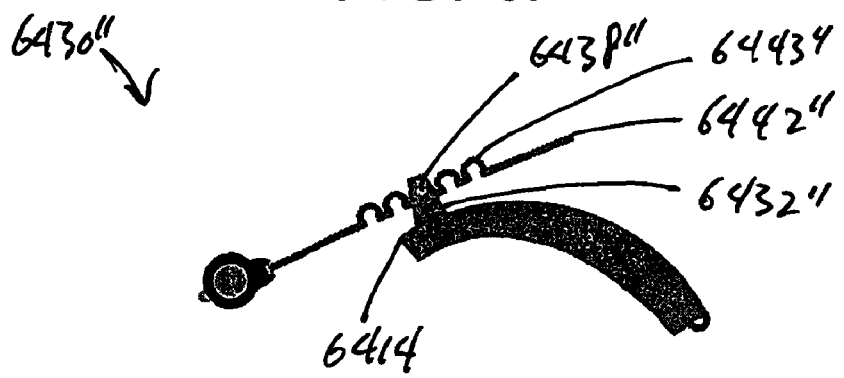

FIGS. 6O-6Q illustrate side views of three different embodiments of a rear bracket 6430, a pair of which help to secure the shoulder frame 6000*b* to the upper-back frame 6000*c*. Referring to FIG. 6O, the rear bracket 6430 comprises a cup 6432 with a hemispherical interior mounted to the back end 6414 of the body of the shoulder pad. The cup 6432 comprises a first opening 6434 opening towards the front. A rear opening 6436 is provided opposite the front opening 6434. Mounted in the cup 6432 is a ball 6440 sized and dimensioned to rotate and pivot therein. A front arm 6442 extends backward from the ball 6440 through the rear opening 6436 of the cup. In the illustrated embodiment, a rear arm 6444 telescopically extends from the front arm 6442. The front 6442 and rear 6444 arms are relatively lockable, thereby providing an adjustable overall length. A sleeve 6446 is mounted to the end of the rear arm 6444 using a ball and socket joint 6448. The sleeve is sized and dimensioned to slidably receive an upper rod 6500 described below. Also illustrated in FIG. 6O is an optional push button locking mechanism 6449 that engages corresponding openings 6502 formed on the upper rod.

FIG. 6P illustrates another embodiment of a rear bracket 643' which is similar to the embodiment illustrated in FIG. 6O. The illustrated embodiment comprises only a single arm 6442' extending between the ball 6440' and the sleeve 6446'. In the illustrated embodiment, the arm 6442' extends through the ball 6440', which comprises a locking mechanism of any type known in the art, for example, a push button lock.

FIG. 6Q illustrates another embodiment of a rear bracket 6430". In this embodiment, a bracket 6432" is mounted towards the rear 6414 of the shoulder pad. A pin 6438" extends laterally from the bracket 6432". An arm 6442" is equipped with a plurality of hooks 6443", which are sized and dimensioned to engage the pin 6438". Applying tension to the structure locks the selected hook 6443" to the pin 6438".

As text viewed in FIG. 6B, the upper-back frame 6000*c* is operatively connected with the shoulder frame 6000*b* through the rear bracket 6430 and the shoulder straps 6450. The upper-back frame 6000*c* comprises an upper rod 6500 slidably mounted to the rear sleeves 6446 brackets. A telescoping vertical rod 6510 is mounted to about the center of the upper rod, for example, using a clip, and extends downwards therefrom. A lower rod 6520 is mounted to the vertical rod 6510 below the upper rod 6500 for example, using clip. The upper 6500 and lower rods 6520 are substantially perpendicular to the vertical rod 6510. Mounted to the upper 6500 and lower 6520 rods, and flanking the vertical rod 6520, is a pair of back plates 6530. Each back plate 6530 comprises a body 6532, which comprises a relatively rigid, strong, and lightweight material, an independently inflatable upper-back chamber 6534. A mount point 6512, for example, an eyelet, is provided at bottom of the vertical rod 6510 to which the shoulder straps 6450 are secured. In the illustrated embodiment, a hip belt 6540 is also mounted to the mount point 6512. As best viewed in FIG. 6C, the hip belt 6540 comprises an adjustable clasp or buckle 6542.

FIG. 6D schematically illustrates a top view illustrating a user's head and the positions of the right 6010*a* and left 6010*b* lateral slats, the rear slat 6020, and the front slat 6030. Left and right lateral slat sleeves 6300 are indicated by open circles. FIG. 7D illustrates the swiveling and alignment mechanism of the neck frame 6000*a* which permits rotational and translational positioning of the user's head. Because the lateral slat sleeves 6300 are positioned on the shoulder pads 6400 (not illustrated in this figure), the distance $w_1$ is constant. Accordingly, and as will become apparent, in some embodiments, no locking mechanism is needed to control the rotational degree of freedom of the lateral slat sleeves 6300. Illustrated in solid is a user's head and neck frame 6000*a* with the user facing forward.

Illustrated in phantom is a user's head and neck frame 6000*a* after a rotation to the right. As shown in the solid lines, the distance between the left lateral slat sleeve 6300*a* and the front slat 6030 is indicated by $d_1$ when the user's head is facing straight ahead. On rotating the head to the right, the distance between the left lateral slat sleeve 6300*a* and the front slat 6030 changes to $d_2$ as the left lateral slat 6010*b* slides forward in the left lateral slat sleeve 6300*b*. Concomitantly, the right lateral slat 6010*a* slides backward in the right lateral slat sleeve 6300*a* to the position indicated because the rear slat sleeves and the front slat sleeves permit sliding of the rear slat 6020 and front slat 6030, respectively, but do not permit rotation. Accordingly, the neck frame 6000*a* is constrained to remain substantially rectangular. Consequently, on rotating the user's head to the right, as indicated in FIG. 6D, the original width $w_1$ between the two rear slat sleeves or the two front slat sleeves changes to the width $w_2$. As discussed above, the rear slat sleeves and front slat sleeves are lockable. Accordingly, when the positions of the rear slat 6020 and front slat 6030 are locked relative to the lateral slats 6010, the resulting rectangle is also locked. If at least one of the lateral slats 6010 were not lockable in a lateral slat sleeve 6300, the rectangle could slide forward and/or backward in the lateral slat sleeves 6300. Providing a locking mechanism for the sliding motion on either the right 6300*a* or left 6300*b* lateral slat sleeves, however, is sufficient to prevent the neck frame 6000*a* from moving. Accordingly, in some embodiments, a locking mechanism for the lateral slat 6010 is provided on only one of the right 6300*a* or left 6300*b* lateral slat sleeves. In other embodiments, locking mechanisms are provided on both.

Those skilled in the art will understand that different arrangements for the neck frame 6000*a* are used in other embodiments, for example, with a different geometry, and/or with more or fewer slats. In some embodiments, the slats form a different shape, for example, a pentagon, hexagon, or another polygon. In some embodiments, at least one of the slats is not generally straight, for example, curved, or a horseshoe shape.

Figure 7A:
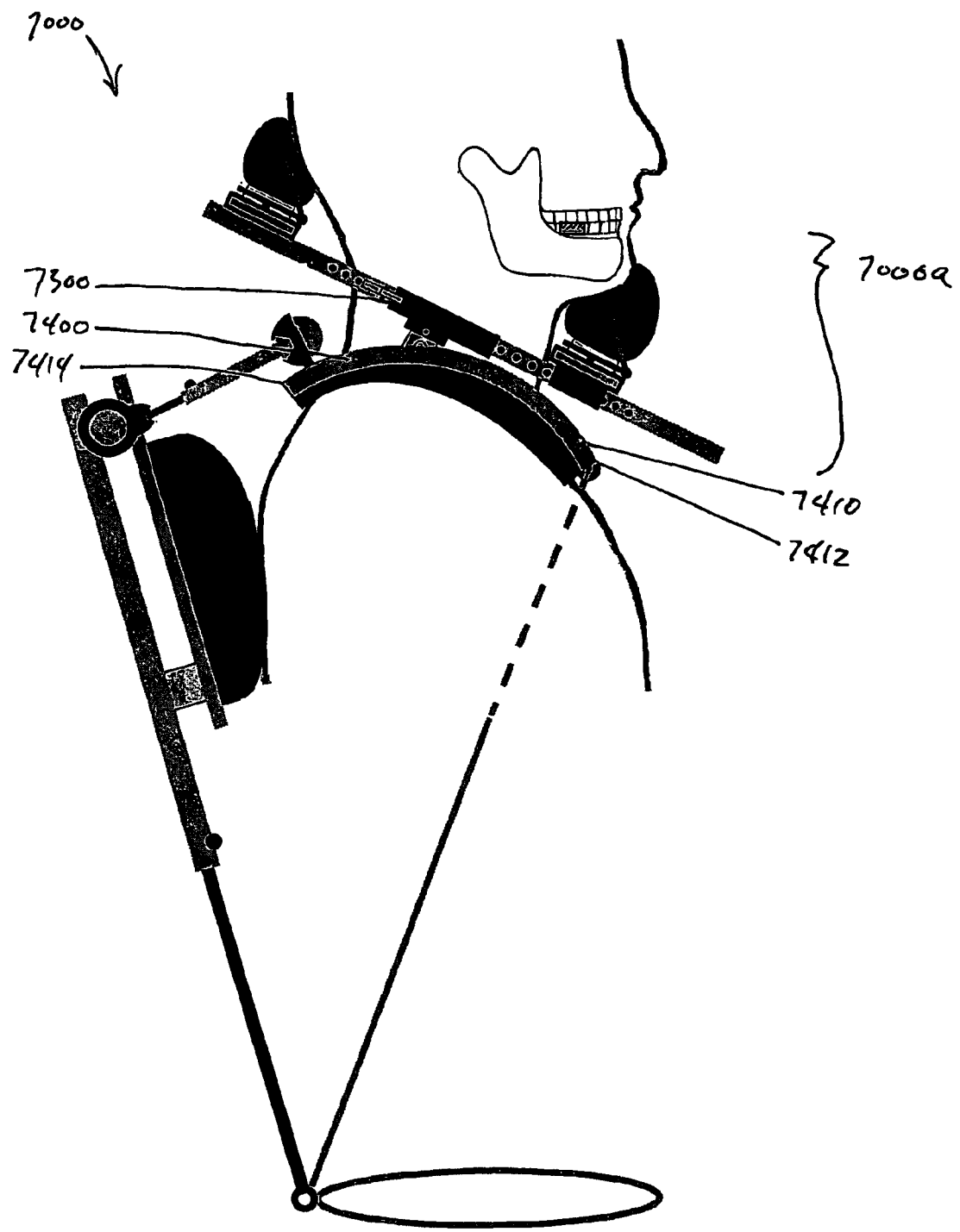
FIGS. 7A and 7B are side and front views, respectively, of an embodiment of a neck-and-upper-back frame that includes a lower cervical tilt.
Figure 7B:
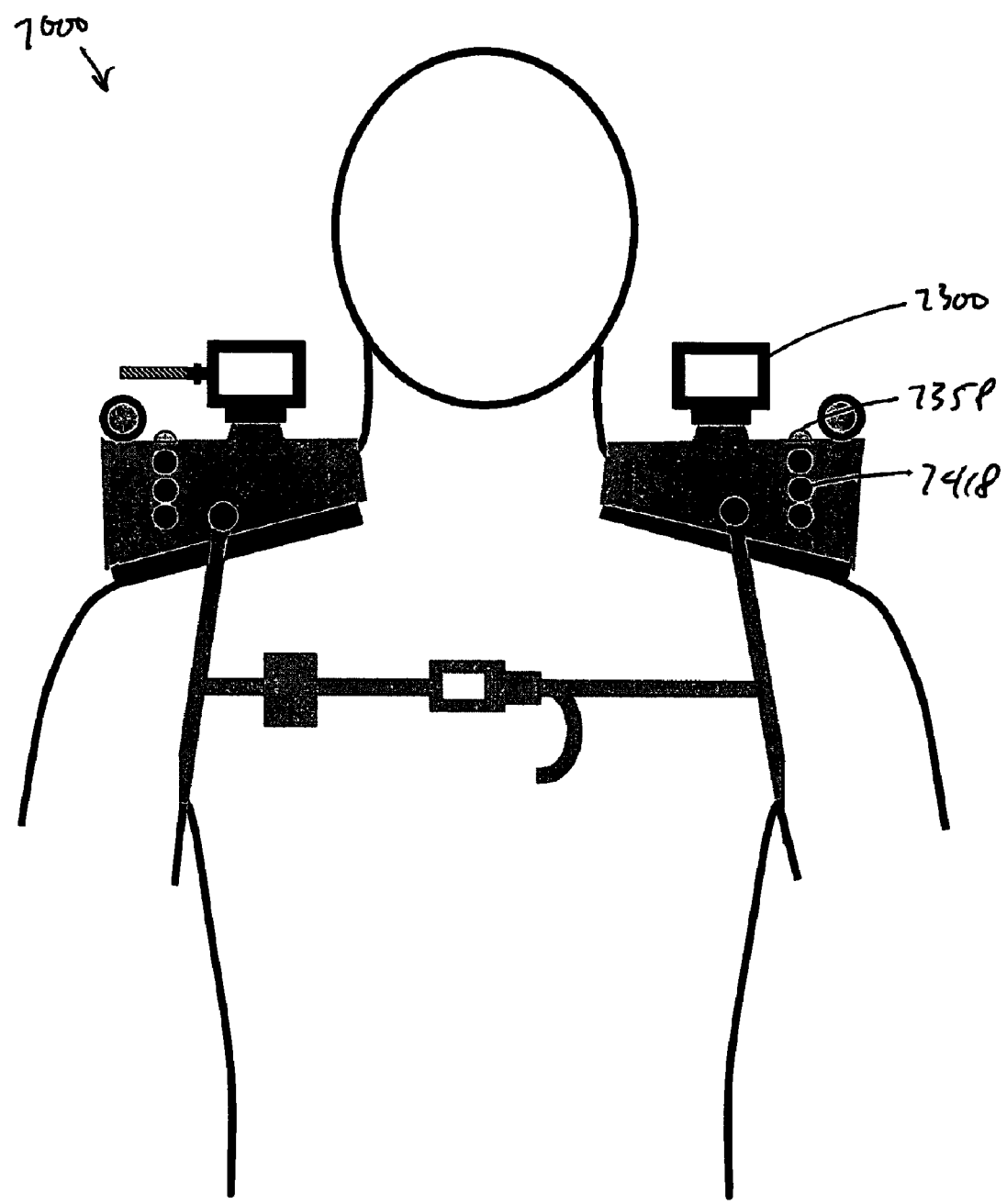
Figure 7B:

The neck frame 6000*a* also provides translational alignment of the head and neck. Front-back alignment is accomplished by sliding the lateral slats 6010 forward or backward in the lateral slat sleeves 6300, and locking at least one of the lateral slat sleeves. Side-to-side alignment is provided by sliding the back 6020 and front 6030 slats in concert in the back 6100 and front 6200 slat sleeves, and locking the back 6100 and front slat sleeves 6200. FIG. 7A and 7B illustrate side and front views, respectively, of another embodiment of a neck-and-upper-back frame 7000. In the illustrated embodiment, the neck frame 7000*a* swivels on the lateral slat sleeves 7300 and has an adjustable lower cervical tilt using a tilting mechanism described below.

Figure 7C:
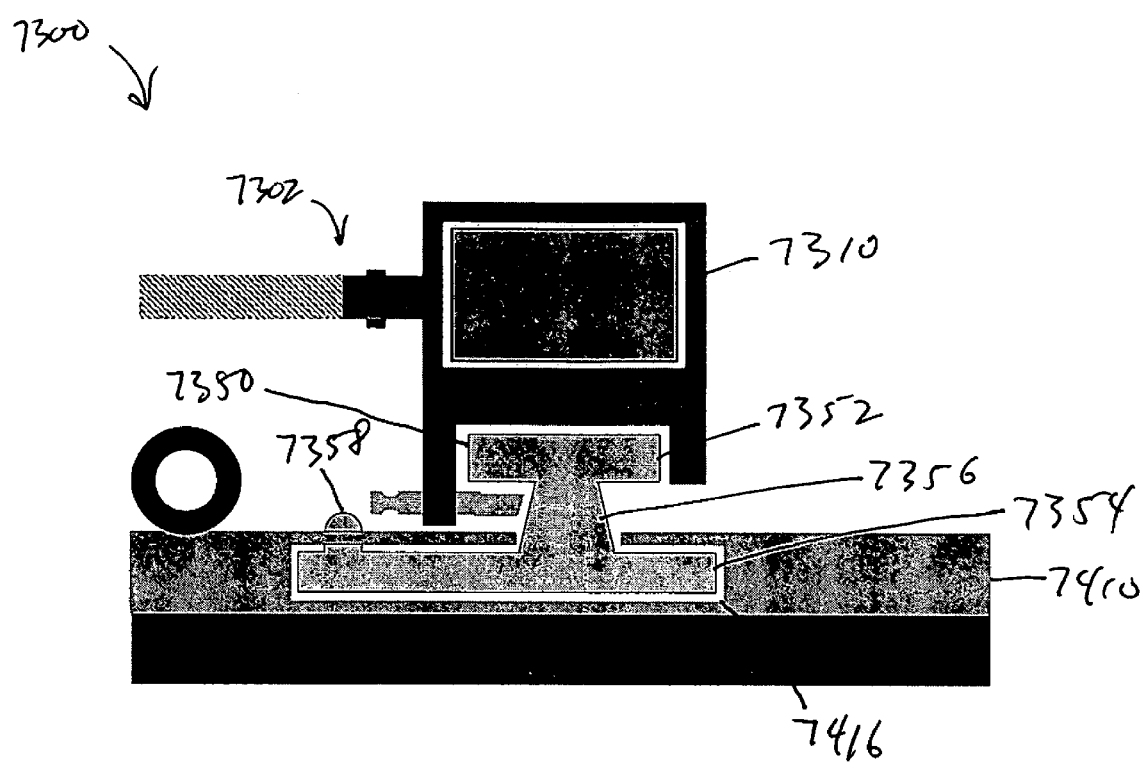
FIG. 7C is a front view of an embodiment of a lateral slat sleeve.

FIG. 7C illustrates a front view of a lateral slat sleeve 7300. The body 7310 and locking mechanism 7302 are substantially similar to the embodiment of the lateral slat sleeve 6300 described above. The tilting lever 7350 is also similar, comprising an enlarged head 7352, shank 7356, and base 7354. The base 7354 is modified compared with the base in the embodiment 6300, however. In the illustrated embodiment, the base 7354 is sized and dimensioned to be slidably received in a channel 7416 formed in the body 7410 of each shoulder pad 7400. In the illustrated embodiment, a push button locking mechanism 7358 is also provided to permit user control of the tilt. The push button 7358 engages suitable holes or openings 7418 (FIG. 7B) provided on the body 7410 of the shoulder pad. A line of openings 7418 extends substantially in parallel with the channel 7416. The channel 7416 extends from the front end 7412 of the frame towards the back end 7414.

In use, the tilting lever 7350 (and lateral slat sleeve 7300) is unlocked by depressing the push button lock 7350. The forward-backward position of the lateral slat sleeve 7300 is adjusted by sliding the base 7354 in the channel 7416, and the position locked when the push button lock 7350 engages the desired opening 7418.

Figure 8A:
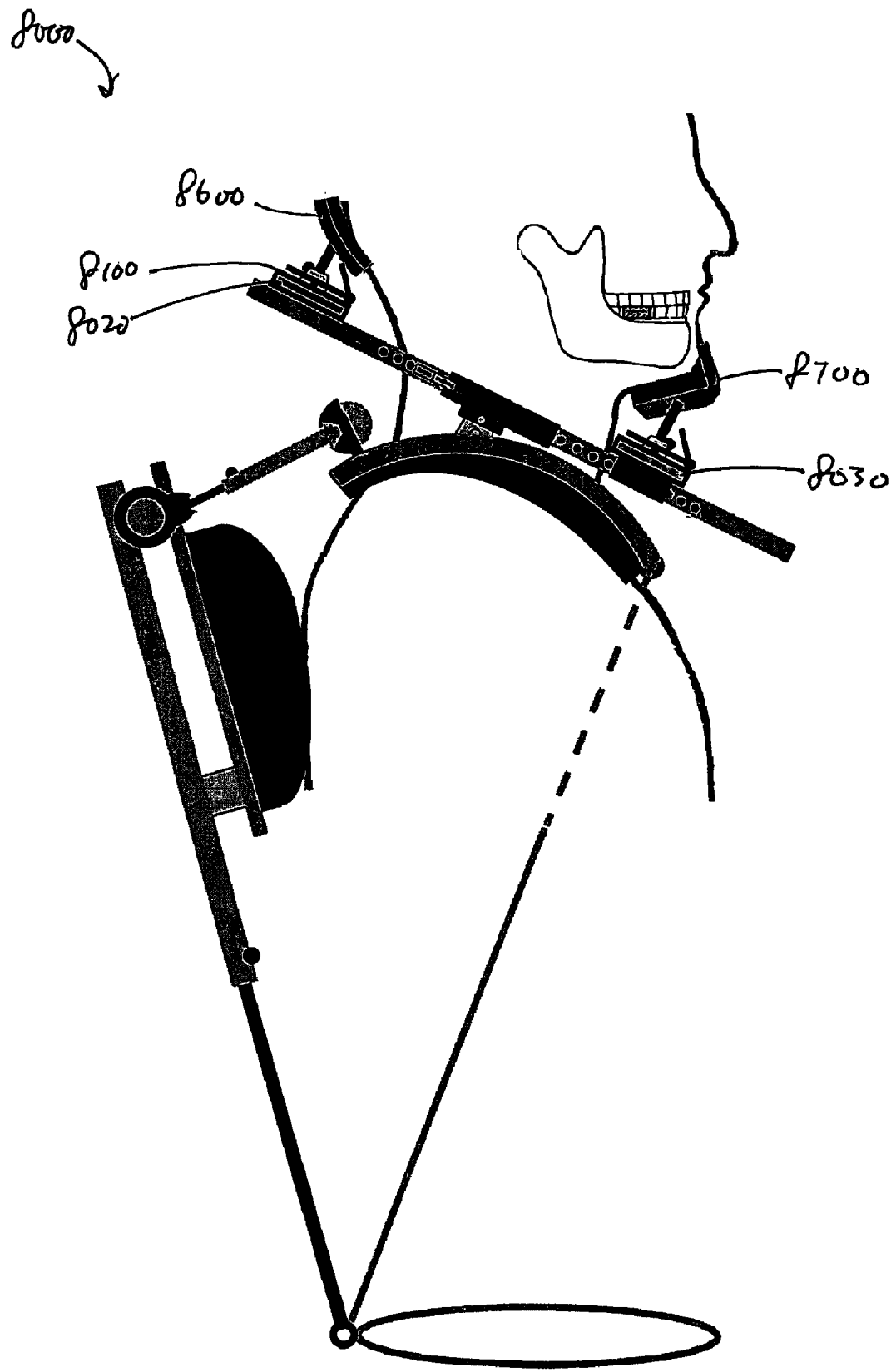
FIGS. 8A and 8B are side and front views, respectively, of an embodiment of a neck-and-upper-back frame that includes a adjustable chin and occipital cups.
Figure 8B:
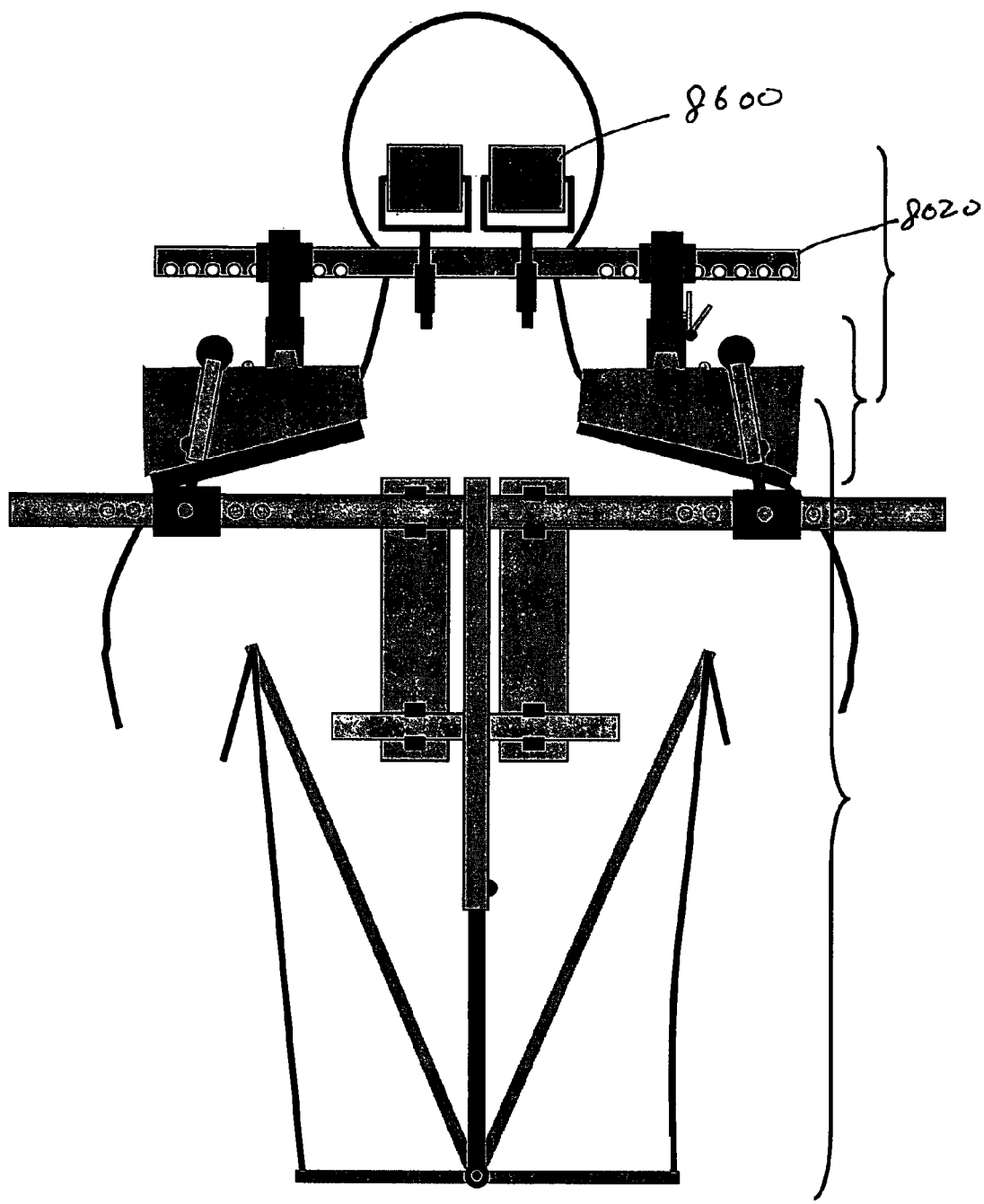

FIGS. 8A and 8B illustrate in side view and back view an embodiment of a neck-and-upper-back frame 8000, which is similar to the embodiment 7000 illustrated and described above, and further comprises adjustable occipital cups and an adjustable chin cup.

In the illustrated embodiment, the height of each occipital cups 8600 is user adjustable. Each occipital cup 8600 is also equipped with self-adjusting swivel and tilt. Similarly, the height of the chin cup 8700 is user adjustable, and equipped with self-adjusting forward and backward tilt. The user controlled and self-adjustment mechanisms are of any suitable type known in the art.

Figure 8C:
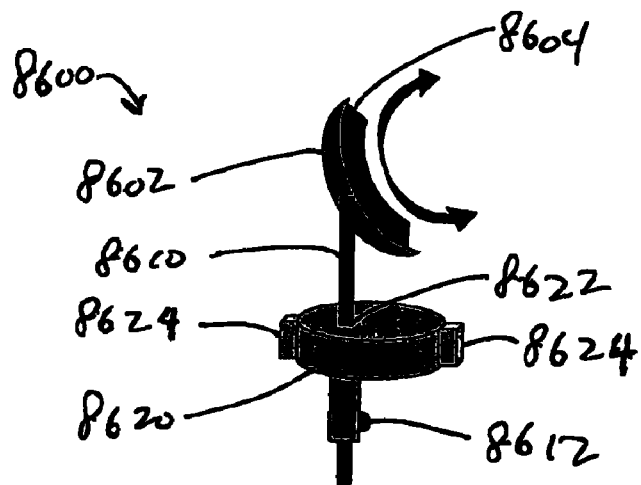
FIGS. 8C, 8D, and 8E are side, back, and top views, respectively of an embodiment of an adjustable occipital cup.
Figure 8D:
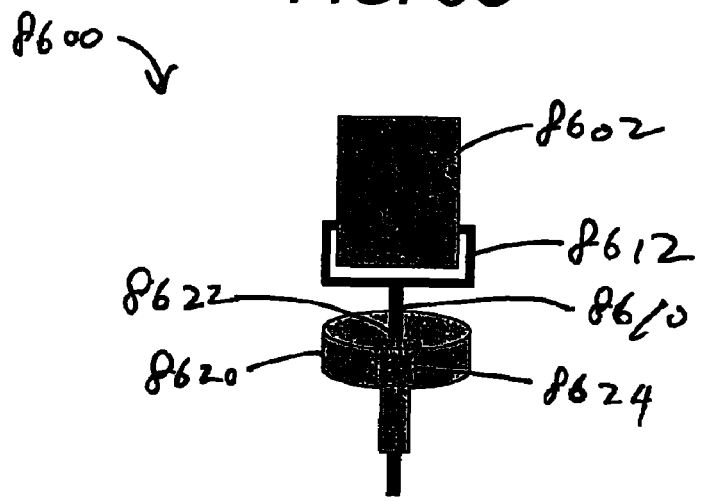
Figure 8E:
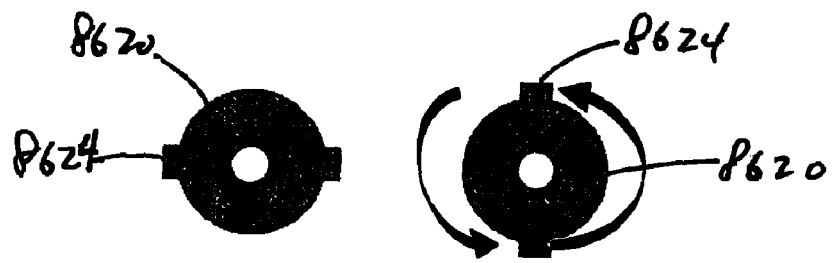

FIGS. 8C and 8D are side and back views, respectively, of an embodiment of an adjustable occipital cup 8600. The occipital cup 8600 comprises a body 8602 in which an inflatable rear chamber 8604 is disposed. As best seen in FIG. 8D, the body 8602 is pivotably mounted to a post 8610 using a pair of pivot arms 8612, thereby providing sagittal tilt as indicated by the arrow in FIG. 8C. The post is, in turn, mounted to a sleeve 8620 comprising an opening 8622 through which the post 8610 is slidable. Height adjustment is provided in the illustrated embodiment using a push button 8612 mounted to the post 8610, which engages corresponding openings on the sleeve 8620. The sleeve 8620 also comprise a pair of tabs 8624, which are sized and dimensioned to engage a radial groove formed in a rear slat as described below. FIG. 8E illustrates top views with arrows illustrating the rotational adjustment of the sleeve 8620.

Figure 8F:
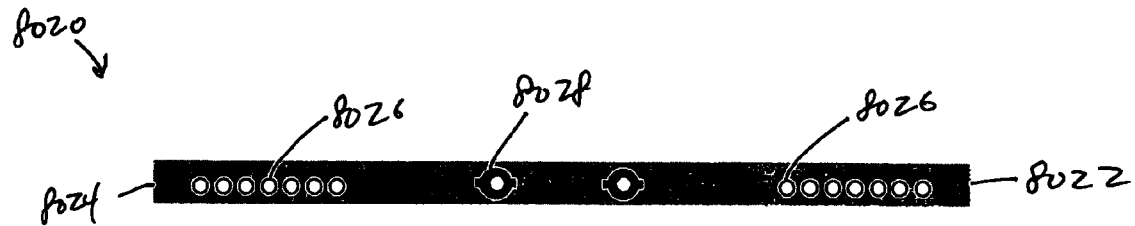
FIGS. 8F, 8G, 8H, and 8I are top, bottom, detail, and cross section views of an embodiment of a rear slat.
Figure 8G:
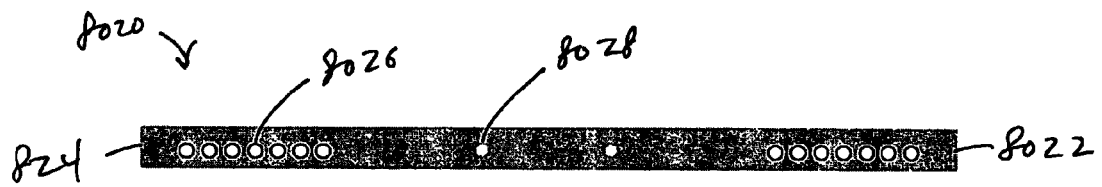
Figure 8H:
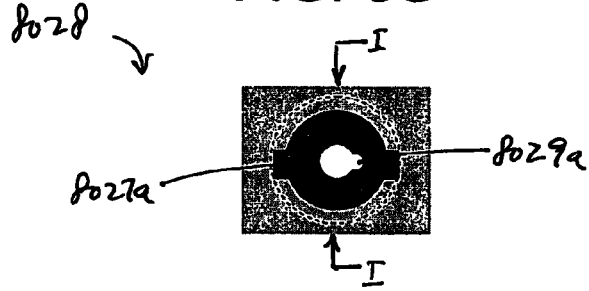
Figure 8I:

FIGS. 8F and 8G are a top view and a bottom view of an embodiment of a rear slat 8020 used in conjunction with the occipital cups 8600. The rear slat 8020 comprises a first or right and 8022 and a second or left end 8024. A series of holes or openings 8026 extends toward the center from either end of the rear slat 8020. The openings 8026 are used in combination with the rear slat sleeve 8000 for locking the rear slat 8020. Near the center of the rear slat 8020 is provided a pair of openings 8028 sized and dimensioned for mounting the sleeves 8620 occipital cups. FIG. 8H illustrates a close up top view of an opening 8028. FIG. 8I is a cross-section of the opening 8028 taken through section I-I in FIG. 8H. As illustrated in FIG. 8I, the opening 8028 comprises a hole 8029 extending through the rear slat 8020, and a radial groove 8027. As shown in FIG. 8H, a pair of notches 8027*a* are provided, which are sized and dimensioned provide access to the radial groove 8027 by the tabs 8624 of the sleeve of the occipital cup 8600. Rotating the tabs 8624 in the radial groove 8027 captures them therein. This arrangement permits the tabs 8624 to rotate freely in the radial groove 8027. In the illustrated embodiment, the hole 8029 comprises a longitudinal groove 8029*a*, which provides clearance for the push button 8612 on the post of the occipital cup 8600.

Figure 8J:
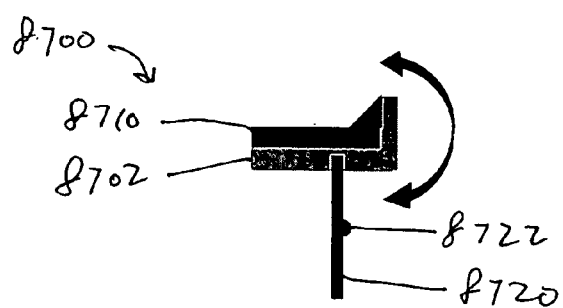
FIGS. 8J and 8K are side and back views respectively of an embodiment of a chin cup.
Figure 8K:
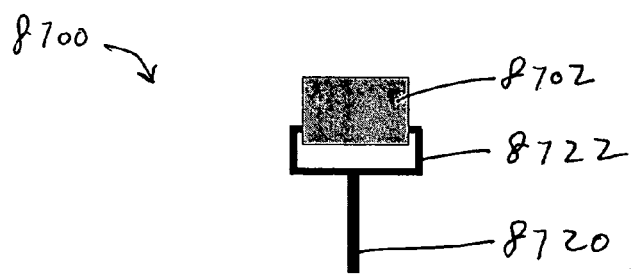

FIGS. 8J and 8K illustrates an embodiment of an adjustable chin cup 8700 which comprises a body 8702 which is in the illustrated embodiment is generally L-shaped. Disposed within the L of the body 8702 is the front air chamber 8710, which is similar to the air chamber 6710 described above. The body 8702 of the chin cup is mounted on a pair of pivot arms 8722, which are in turn mounted to a post 8720, thereby providing a self-adjusting sagittal tilt as indicated by the arrows in FIG. 8J. The post 8720 is sized and dimensioned to be received in a sleeve mounted on a front slat 8030, as discussed below. Height adjustment is provided through a push button 8722 that cooperates with a corresponding opening in the sleeve, described below. Other embodiments use other adjustment means are known in the art.

Figure 8L:
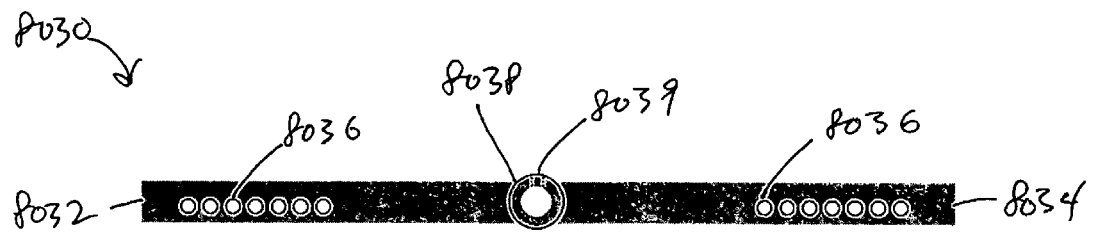
FIGS. 8L and 8M are top and side views of an embodiment of a front slat.
Figure 8M:
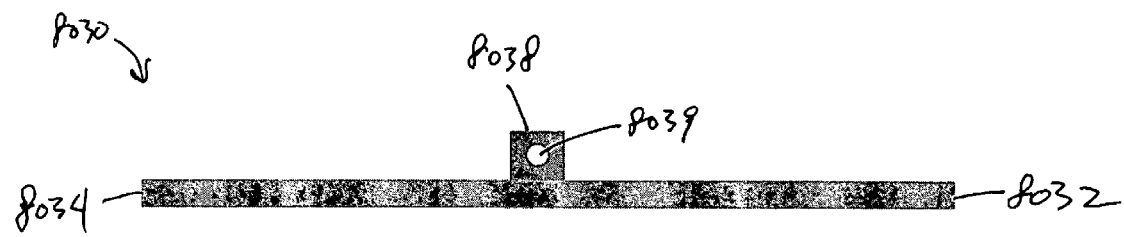

FIGS. 8K and 8L are top and front views respectively of an embodiment of the front slat 8030 used with the chin cup 8700. The front slat comprises a first or right end 8032 and a second or left end 8034. A plurality of openings or holes 8036 extend from either end towards the center, which are used in conjunction with the front slat sleeve 8200 to lock the front slat 8030 in position. A sleeve 8038, which is sized and dimensioned to receive the corresponding post 8720 on the chin cup, is mounted at about the center of the top of the front slat 8030. An opening 8039 is provided at the front of the sleeve 8030 that engages the corresponding push button 8722 on the post of the adjustable chin cup, which provides height adjustment.

Figure 9A:
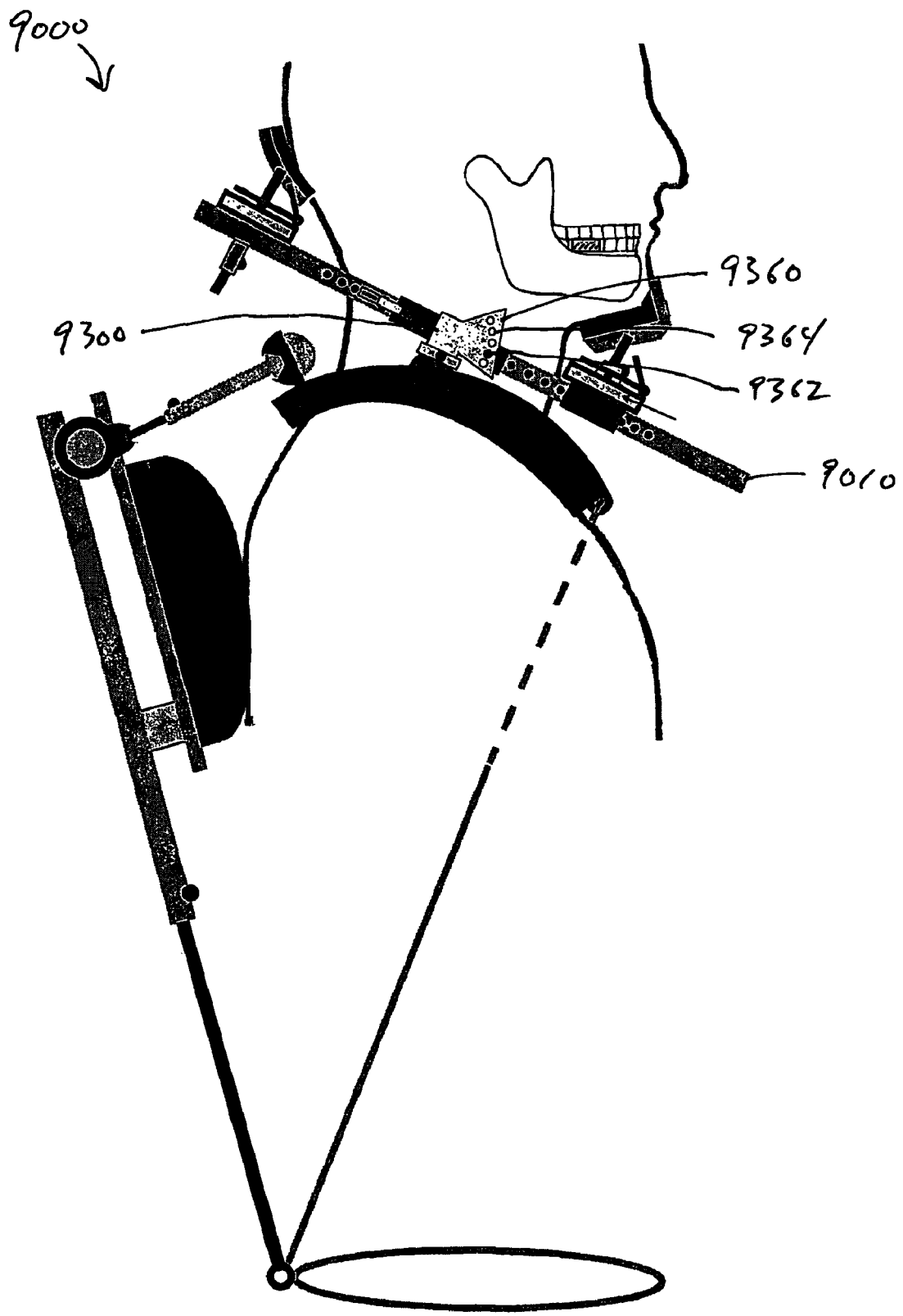
FIGS. 9A and 9B are side and front views, respectively, of an embodiment of a neck-and-upper-back frame that includes a middle cervical tilt.
Figure 9B:
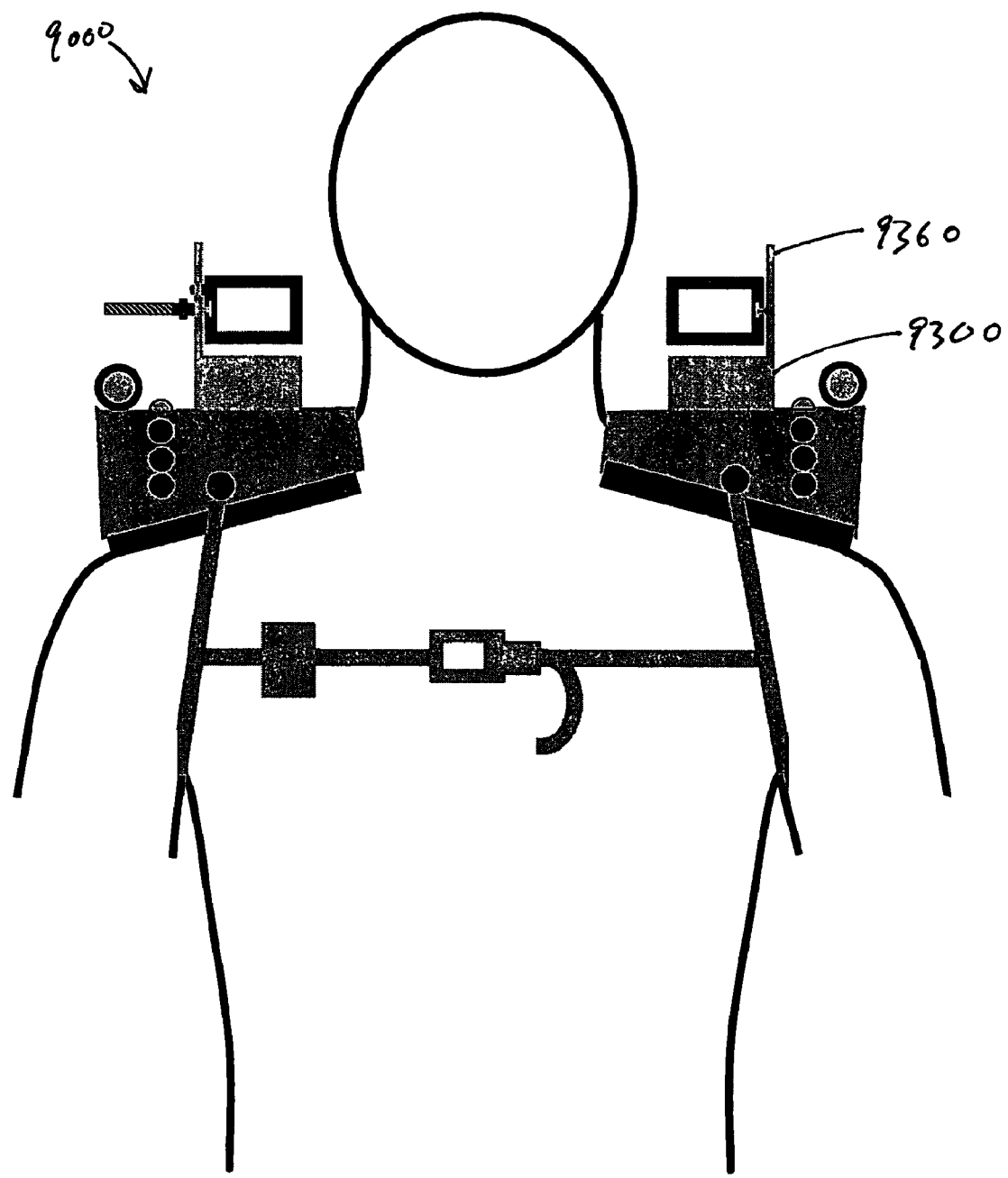
Figure 9B:

Another embodiment of the neck-and-upper-back frame 9000 illustrated in FIGS. 9A and 9B in side view and front view, respectively. The embodiment 9000 is similar to the embodiment 8000 described above, with the addition of a middle cervical tilt feature described below. As best seen in FIG. 9A, the lateral slat sleeve 9300 includes a middle tilt locking mechanism, which permits the user to tilt the lateral slats 9010 upwards and downwards.

Those skilled in the art will understand that other embodiments provide adjustability of the either of the occipital cups 8600 and/or chin cup 8700 using different means, configurations, or structures know in the art, for example, ball joints, hinges, screws, racks-and-pinions, gears, resilient structural and/or support members, fluid-filled pistons, combinations thereof, and the like. Furthermore, those skilled in the art will understand that either of the occipital cups 8600 and/or chin cup 8700 has a different shape and/or dimensions in other embodiments.

Figure 9C:
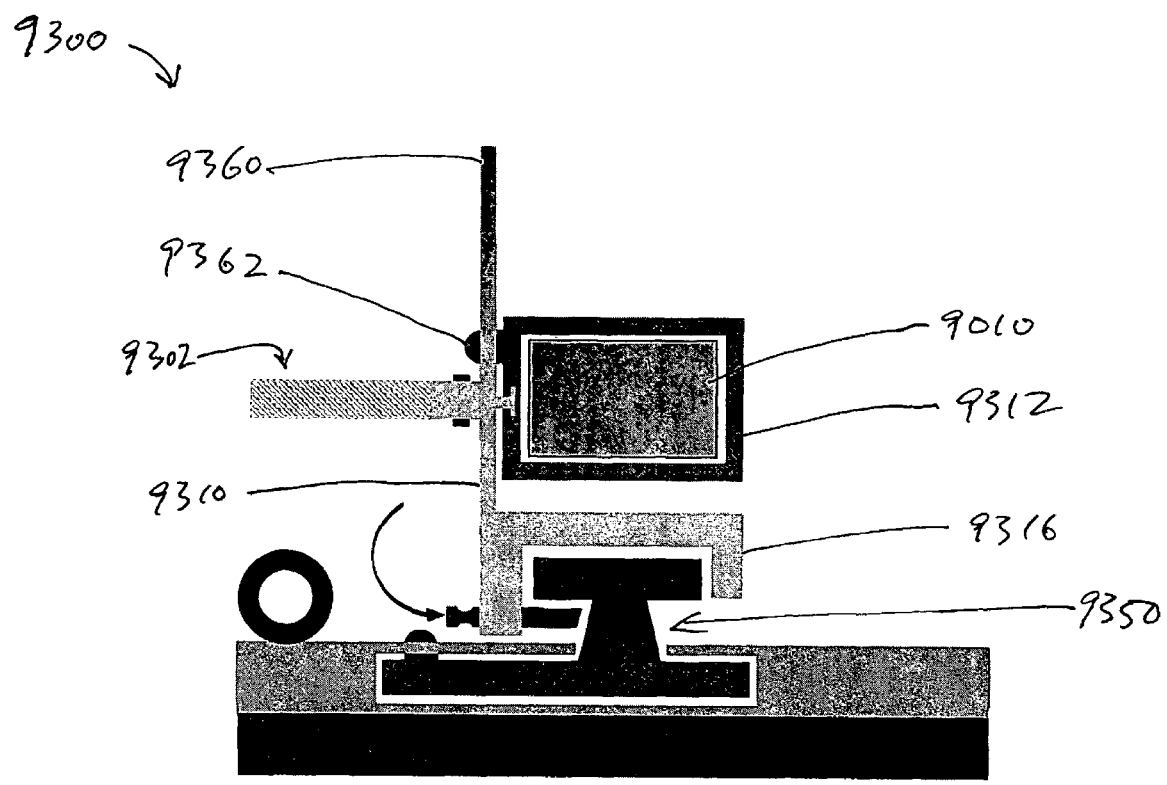
FIG. 9C is a front view of an embodiment of a lateral slat sleeve.

FIG. 9C illustrates a front view of a lateral slat sleeve 9300 implementing a middle cervical tilt feature. The lateral slat sleeve 9300 comprises a body 9310 at the lower portion of which is formed a bushing 9316, which is substantially similar to the bushings described above in the embodiments of the lateral slat sleeves 6300 and 7300. The arrangement of the tilting lever 6350 is similar to the tilting lever of the embodiment of the lateral slat sleeve 7300 described above.

The body 9310 comprises a pivot and locking plate 9360 extending from a side of the bushing 9316, such that the faces of the plate 9360 face left and right, as illustrated in FIG. 9A. A channel 9312 is pivotably mounted to the plate 9360 to provide a middle cervical tilt. The channel 9312 is sized and dimensioned to slidably receive a lateral slat 9010 therethrough. A lever and plunger locking mechanism 9302 is provided for locking the sliding motion of the lateral slat 9010 in the channel 9312. The channel 9312 is equipped with a push button locking mechanism 9362 that cooperates with a plurality of holes or openings 9364 formed on the plate to lock the up and down pivoting motion of the middle cervical tilt. Those skilled in the art will understand that the openings 6364 are disposed at a substantially constant radius from the middle-tilt pivot point.

Each of the neck-and-upper-back frames 6000, 7000, 8000, and/or 9000 comprises one or more features that are independently applicable and/or combinable in other embodiments. For example, the embodiment 6000 includes a swiveling neck frame that permits rotational and translational alignment of the head. The swiveling neck frame feature is present on each of the disclosed embodiments. The embodiment 7000 includes a lower cervical tilt feature, implemented using adjustable tilt levers that are longitudinally adjustable on the shoulder pads. The embodiment 8000 includes the lower cervical tilt feature, as well as adjustable occipital and chin cups. The embodiment 9000 adds a middle cervical tilt feature to the embodiment 8000 implemented in the lateral slat sleeves. Each of these embodiments also includes other features. Those skilled in the art will understand that some embodiments implement the features of the neck-and-upper-back frames 6000, 7000, 8000, and/or 9000, in different combinations.

Each of the disclosed neck-and-upper-back frames comprises seven air chambers. The neck frame comprises a left and a right rear chamber, each engaging the corresponding left and right occipital regions of the head (also referred to herein as "occipital processes," "occipital protuberances," or "occipital regions"), and a front chamber disposed under the user's chin. The shoulder frame comprises a left and a right shoulder chamber. The upper-back frame comprises a left and a right upper-back chamber. Each of the air chambers comprises a suitable flexible and gas tight material known in the art, for example, a polymer, natural rubber, synthetic rubber, combinations thereof, and the like. In some embodiments, the material is a composite, for example, fibers and/or fabric impregnated with and/or covered with a flexible and gas tight material. In some embodiments, the material is elastomeric. Suitable materials for air chambers are discussed in greater detail above. Each air chamber includes one or more inflation ports through which the air chamber is inflated and/or deflated. Fluidly connecting an inflation port with a source of pressurized gas causes an air chamber to inflate, and fluidly opening an inflation port to ambient or sub-ambient pressure causes the air chamber to deflate.

Those skilled in the art will understand that in some embodiments, pressurized gas is supplied to one or more of the inflation ports of the air chambers through tubing fluidly connected to one or more manifolds of any suitable type known in the art. The tubing is of any suitable type known in the art, for example, rubber, vinyl, silicone, plastic, metal, combinations thereof, and the like. In some embodiments, the deflation of one or more of the air chambers is also implemented using one or more manifolds. In some preferred embodiments, the inflation and deflation all of the air chambers are controlled using a manifold. The manifold is user controlled, automated, or a combination thereof. In some preferred embodiments, the manifold is automated, for example, controlled by a computer, microprocessor, embedded processor, or the like. In some embodiments, a user generated pressurized gas, for example, a hand bulb, hand pump, or foot pump, is used to inflate at least one of the air chambers. In some embodiments, a non-user generated pressurized gas is used to inflate at least one of the air chambers, for example, a mechanical air pump, compressor, or compressed gas cylinder. In some preferred embodiments, the manifold is supplied using a non-user generated pressurized gas.

In some embodiments, the manifold independently controls the inflation state of each of the air chambers. In some embodiments, the inflation state of some of the air chambers is controlled together at least some of the time.

Figure 10:
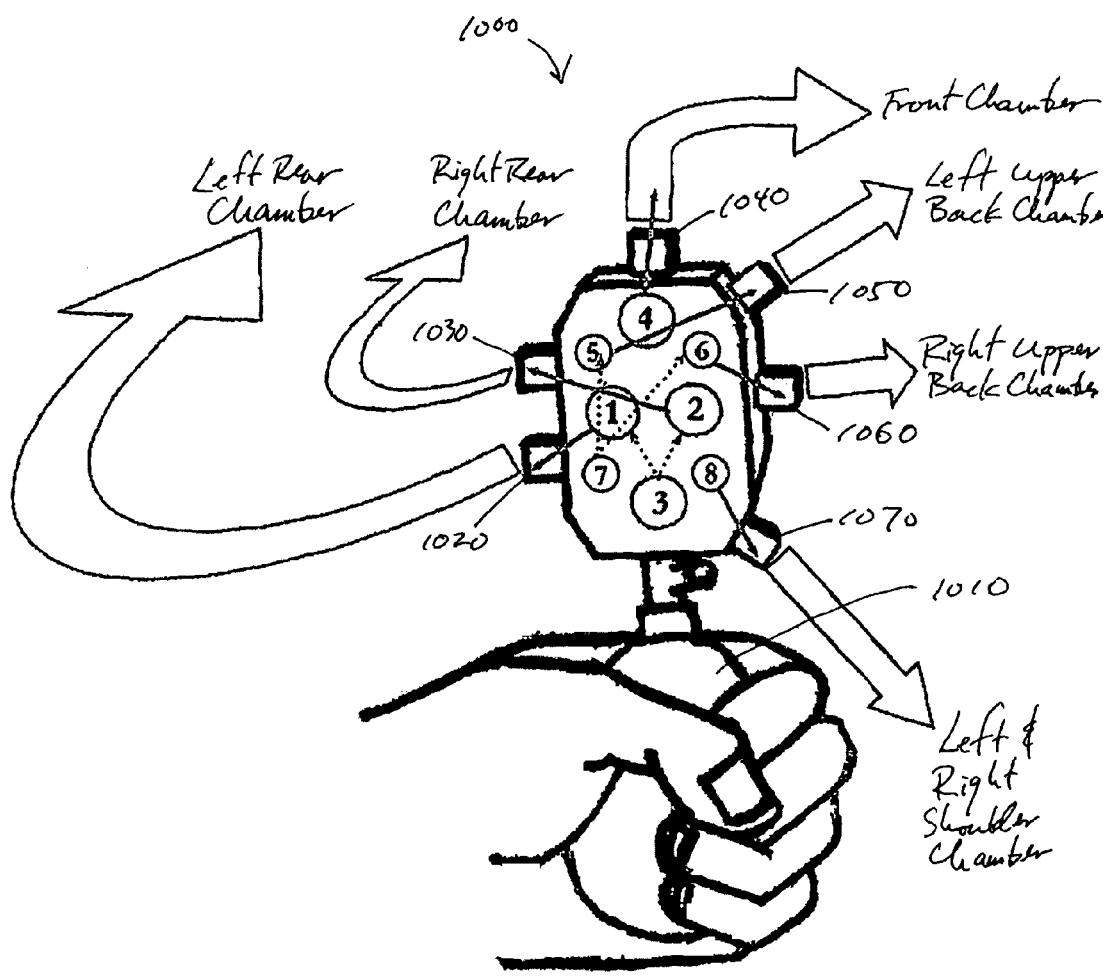
FIG. 10 illustrates in perspective view an embodiment of a manually operated manifold and gas bulb.

FIG. 10 illustrates an embodiment of a user controlled manifold 1000 and source of pressurized gas 1010 in fluid connection therewith suitable for use with some embodiments of the disclosed neck-and-upper-back frames and methods disclosed herein. In the illustrated embodiment, the source of pressurized gas 1010 is a hand bulb. The manifold comprises a plurality of manually activated valves of any suitable type, labeled 1-8 in FIG. 10, each of which control the inflation of one or more of the air chambers. The gas exits the manifold 1000 through a plurality of outlet ports 1020, 1030, 1040, 1050, 1060, and 1070. The correspondence between the valves, outlet ports, and air chambers for the illustrated embodiment is provided in TABLE I. In the illustrated embodiment, the shoulder air chambers are inflated together rather than separately. Those skilled in the art will understand that other arrangements for the manifold, and the control scheme are used in other embodiments.

TABLE I

| Valve | Outlet Port | Air Chamber |
|---|---|---|
| 1 | 1020 | Left Rear |
| 2 | 1030 | Right Rear |
| 3 | 1020 and 1030 | Left and Right Rear |
| 4 | 1040 | Front |
| 5 | 1050 | Left Upper Back |
| 6 | 1060 | Right Upper Back |
| 7 | 1050 and 1060 | Left and Right Upper Back |
| 8 | 1070 | Left and Right Shoulder |

Each of the disclosed neck-and-upper-back frames is also useful for implementing embodiments of the method 400 for spiral traction described above. The following description of the method references certain of the disclosed embodiments of the nec-and-upper-back frame, but those skilled in the art will understand that the methods are also applicable to other embodiments.

In step 410, the neck-and-upper-back frame 6000 is positioned and secured to the patient. In some embodiments, the shoulder 6000b and upper-back 6000c frames are first positioned and secured to the patient to provide the state illustrated in FIG. 6C. The shoulder 6000a and upper-back 6000c frames are first assembled and put on and worn by the user in much same way that a jacket is.

The shoulder pads 6400 are positioned on the patient's shoulders. Referring to FIG. 6B, the distance between the sleeves 6446 of the rear brackets is adjusted on the upper rod 6500 of the upper-back frame 6000c according the patient's shoulder width. The lengths of the rear brackets 6430 are adjusted to match the tilt of the upper-back frame 6000c to the tilt of the lower thoracic spine. There should be a small space between the upper-back chambers 6534 and the spine. The length of the vertical rod 6510 is adjusted to the patient's waist. The chest strap 6460 and hip belt 6540 are adjusted and secured. In embodiments comprising adjustable tilting levers (7000, 8000, and 9000), the tilting levers are adjusted and locked in their rearmost positions.

The neck frame 6000a is then assembled. The lateral slats 6010 are slid through the lateral slat sleeves 6300, and the rear 6020 and front 6030 slats mounted on the lateral slats 6010 using the rear slat sleeves 6100 and front slat sleeves 6300, respectively. The occipital cups 6600 are mounted to the rear slat 6020. The chin cup 6700 is mounted to the front slat 6030.

The neck frame 6000a is mounted to the shoulder frame 6000b by engaging the bushings 6316 of the lateral slat sleeves to the heads 6352 of the tilting levers, and the retaining pins 6318 inserted. The positions of the occipital cups 6600 are adjusted such that the rear chambers engage the patient's occipital regions of the head, for example, by adjusting the forward positions of the lateral slats 6010 in the lateral slat sleeves 6300, and/or using the lower cervical tilt in embodiments with this feature, and/or adjusting the heights of the occipital cups in embodiments with this feature. TMJ spacers 300 (FIG. 6A) are inserted and positioned in the patient's mouth. The use and benefits of the TMJ spacers 300 are discussed in above. The position of the chin cup 6700 is adjusted such that the front chamber contacts the chin and extends about halfway to the angle of the mandible, for example, by adjusting the height of the chin cup in embodiments with this feature. In some embodiments, the front chamber is inflated to contact the user's chin, for example, where the chin cup is not adjustable.

In step 420, the spine is aligned. Each of the disclosed embodiments of the neck-and-upper-back frame permit the alignment of the cervical vertebrae, and at least some of the thoracic vertebrae. The disclosed devices permit orientation of the spine in any direction along the sagittal, coronal, and transverse directions prior to the application of axial traction to the spine. The following describes a preferred and non-exclusive embodiment for aligning the spine.

The neck frame permits rotational and translational positioning and alignment of the patient's head, as discussed above and illustrated in FIG. 6D. In this step, the pre-traction rotation of the neck frame is adjusted as discussed above.

The lower pre-traction tilt is then adjusted for extension or flexion as desired. In embodiments with a lower cervical tilt feature, the positions of the tilting levers 7350 (FIG. 7C) are adjusted on the shoulder pads 7400 using the push button 7358 and openings 7418 (FIG. 7B) as discussed above. In embodiments with middle cervical tilt, the tilt of the channels 9312 (FIG. 9C) is adjusted using the push button 9362 and corresponding opening 9364 of the lateral slat sleeve 9300, as discussed above. In some embodiments, the lower pre-traction tilt is adjusted by inflating the rear and/or front chambers. The side pre-traction tilt is adjusted using the rear chambers.

In step 430, traction is applied using the air chambers of the neck frame 6000a (front, right rear, and left rear). In some embodiments of this step, the patient is in different positions, for example, standing, sitting, reclining, lying down, etc.

In some embodiments, the shoulder chambers 6420 are inflated, which stretches the neck downward, thereby stretching the trapezius muscles. In some embodiments, the upper-back chambers 6534 permit user controlled flexion, extension, rotation, and lateral flexion of the upper back. For example, in some embodiments, the left or right upper-back chamber 6534 is inflated to rotate the upper back to correct rotational scoliosis. Inflating one the right or left upper-back chambers 6534 produces both rotation and lateral flexion in the thoracic spine due to the coronal orientation of the facet joints in this area of the spine. These steps are optional when the traction is repeated as discussed below.

Some embodiments comprise steps of axial distraction of the neck simultaneous with one of extension, flexion, or lateral flexion. In preferred embodiments, one of the spiral traction sequences described above (circular or figure-eight) is then applied using the air chambers of the neck frame 6000a.

In step 440, the neck frame air chambers are then deflated.

In step 450, steps 430 and 440 are optionally repeated one or more times. Repeated step(s) 430 uses the same and/or a different sequence. In some preferred embodiments, the spiral traction sequence is the figure-eight sequence, which is repeated once or twice.

It is believed that in selectively stretching of the neck in any of four separate directions, embodiments of the disclosed devices, systems, and methods provide a combination of at least some of the following benefits: relaxing muscle spasms; releasing muscle contractures; releasing scar-tissue adhesions; improving circulation of blood, lymph, and cerebral-spinal fluid; draining edema surrounding muscles and joints; decompressing spinal-joints; promote healing of spinal-joint cartilage; comfortably and effectively increasing intervertebral disc-height; promoting healing of intervertebral disc tears; restoring alignment of cervical and/or upper-thoracic spinal-joints; reducing thoracic kyphosis and/or rotational scoliosis; decompressing spinal nerve-roots and/or brachial nerves; and/or improving TMJ function. Without being bound by any theory, it is believed that combinations of the following mechanisms provide these benefits.

Releasing Tight Muscles:

Lengthen Contracted Muscle Fibers: Muscle fibers lengthen as the neck is stretched in four separate directions from any position.

Release Reflex Muscle Spasms: Stretching a muscle triggers the "stretch-reflex," which tends to contract that muscle; however, the antagonistic muscle group, which remains stationary, relaxes by reciprocal reflex innervation. Hence, muscle spasms relax by stretching one side of the neck while the other side is stationary. The neck tilting provided herein effectively stretches at least the following muscles and muscle groups:

Muscles Stretched with Side-Tilt: Sterno-cleido-mastoid, scalenes (ant. med. post.), splenius capitis, levator scapulae, multifidus, suboccipital muscles, obliquus capitis superior, obliquus capitis inferior.

Muscles Stretched with Forward-Tilt: Suprahyoid muscles, digastric (post. belly), stylohyoid, trapezius (vertical fibers), semispinalis capitis, suboccipital muscles, rectus capitis posterior major, rectus capitis posterior minor.

Muscles Stretched with Back-Tilt: Platysma, suprahyoid muscles, digastric (ant. belly), mylohyoid, infrahyoid muscles, omohyoid, sternohyoid, thyrohyoid.

Prevent Muscle Spasms During Traction: Spasm of the posterior cervical musculature and of the masseter muscle secondary to TMJ irritation is avoided in some embodiments during traction by the disclosed mechanisms that decompress the TMJ using the disclosed TMJ spacers.

Promoting Healing and Flexibility of Connective Tissue

Releasing Scar Tissue Adhesions: Adhesions that form with surgery, injury, or repetitive motion in different planes of the connective tissue fascia are released by stretching the neck from different positions and in four separate directions.

Reducing Bulging Spinal Discs: Bulges in torn spinal discs are reduced as scar tissue adhesions that form in different planes around the spinal discs are released by stretching the neck from different positions and in four separate directions.

Decompress Joint Cartilage: Cartilage on the surface of spinal joints is decompressed as adhesions formed in different planes on the joint capsule are released by stretching the neck from different positions and in four separate directions.

Promoting Circulation of Bloods Lymph, and CSF and Reducing Local Tissue Edema

Improve Flow of Blood and Lymph: Blood flow is increased in the small capillaries and lymph flow is increased into the lymphatic vessels as tight muscles and scar tissue that obstructs flow is released.

Drain Local Tissue Edema: Inflammatory and metabolic-waste fluids trapped around spinal joints, nerves, and myofascial "Trigger Points" drain more easily as tight muscles and scar tissue obstructing flow is released.

Improve Circulation of Cerebral Spinal Fluid (CSF): Flow of cerebral spinal fluid in the brain and spinal cord is promoted as muscles in the suboccipital area of the neck relax and stagnant fluid drains.

Promoting Healing of Nerve Tissue

Releasing Nerve Root Entrapment. Mechanical entrapment of nerve roots is reduced as muscles and scar tissue are released.

Releasing Peripheral Entrapment of Brachial Nerves. Mechanical entrapment of peripheral nerves in the neck, chest, and wrist is reduced as the "Linked-Chain" of muscles that extends from the neck to the shoulder, chest, elbow, wrist, and fingers relax in succession.

Promoting Correct Spinal Alignment

Spinal joint alignment and range of motion improves as muscle tone is balanced, adhesions are reduced, blood flow is promoted, inflammation is reduced, and spinal joint cartilage, discs, and nerves heal.

It is believed that at least some of these and/or other benefits are useful in treating a variety of conditions. The following is a non-exclusive list of conditions treatable using the disclosed devices, systems, and methods.

Whiplash, Spinal Disc Injury, and Osteoarthritis (degenerative joint disease or DJD): Lengthening contracted muscles, releasing soft tissue adhesions, improving blood flow, and reducing inflammation promotes healing of spinal discs and spinal-joint cartliage.

Headaches and Fibromyalgia: Releasing muscle spasms and soft tissue adhesions helps to improve blood flow, drain metabolic waste-fluids, and decompress nerve endings for pain relief in tension-headaches and chronic myofascial "Trigger-Point" Syndromes.

Thoracic-Outlet and "Multiple-Crush" Carpal-Tunnel. These benefits are generally observed in the disclosed neck-and-shoulder-fame systems. Releasing the scalene, rhomboid, and pectoralis minor muscles helps to release nerve compression of the brachial plexus of nerves and of the subclavian artery. The brachial plexus of nerves can be compressed in the neck neck as it passes between the anterior and middle scalene muscles. Stretching the scalene muscles releases compression of the brachial plexus in the neck. The brachial plexus of nerves can be compressed in the chest as it passes underneath the pectoralis minor muscle. Stretching the pectoralis minor muscle by expanding the chest, and lowering the scapula (shoulder-blade) by relaxing posterior neck muscles (e.g., trapezius, rhomboids), releases compression of the brachial plexus in the chest. The brachial plexus of nerves can be compressed in the wrist as the median nerve passes through the carpal tunnel. Relaxing posterior neck muscles lowers the scapula and relaxes the biceps brachii muscle, which originates from the front of the scapula and inserts into the fascia of the wrist flexor muscles at the elbow; as a result, the wrist flexor muscles relax, helping to release compression of the brachial plexus in the wrist.

Thoracic Kyphosis and Rotational Scoliosis: These benefits are generally observed in the disclosed neck-and-shoulder-fame systems. Extending and rotating the upper-thoracic spine helps to reduce kyphosis and scoliosis.

TEMPORO-MANDIBULAR JOINT SYNDROME (TMJ): Stretching and relaxing the suprahyoid and infrahyoid muscles helps to reduce pain and crepitus (clicking) in the TMJ. The suprahyoid muscles attach to the temporal bone or to the jaw (mandible), and control the TMJ directly. The infrahyoid muscles control the TMJ indirectly through the suprahyoid muscles and their common attachment at the floating hyoid bone in the front of the neck. The stylohyoid and the digastric (posterior belly) suprahyoid muscles attach to the temporal bone. They are stretched and relaxed with forward tilt of the neck. The mylohyoid and the digastric (anterior belly) suprahyoid muscles attach to the mandible Oaw). They are stretched and relaxed with back tilt of the neck. The omohyoid, thyrohyoid, and sternohyoid infrahyoid muscles affect the TMJ indirectly thru the suprahyoid muscles with which they share the floating hyoid bone as a common point of insertion. They are stretched and relaxed with back tilt of the neck.

Central Nervous (CNS) System Conditions: The pumping action created by stretching the upper-cervical and suboccipital-areas in any direction improves the flow of blood and CSF to the brain, and the flow of waste-fluids away from the brain, thereby decompressing and revitalizing the CNS nerve tissue. Case studies published by Dr Erin Elster have shown that improving upper-cervical alignment following a neck injury helps to improve neurologic conditions that are sometimes associated with neck trauma such as multiple sclerosis, Parkinson's, trigeminal neuralgia, torticollis, tremors, bipolar disorder, attention deficit disorder, seizures, Alzheimer's and vertigo (Elster, *J. Vertebral Subluxation Res.* 2001, 4(2)22-29, the disclosure of which is incorporated by reference.)

The embodiments illustrated and described above are provided as examples of certain preferred embodiments. Various changes, modifications, substitutions can be made to the embodiments presented herein by those skilled in the art without departure from the spirit and scope of this disclosure, the scope of which is limited only by the claims appended hereto.

Those skilled in the art will understand that changes in the devices, systems, and/or methods described above are possible, for example, adding and/or removing components and/or steps, and/or changing their orders. While the above detailed description has shown, described, and pointed out novel features as applied to various embodiments, it will be understood that various omissions, substitutions, and changes in the form and details of the device or process illustrated may be made by those skilled in the art without departing from the spirit of this disclosure. As will be recognized, some embodiments do not provide all of the features and benefits set forth herein, and some features may be used or practiced separately from others.

What is claimed is:

1. A cervical traction system having a C-shaped extensible multi-chambered cervical collar removably coupleable to a user, comprising:

a front and a back,
a right end and a left end defining a back opening;
a bottom section comprising an extensible bottom chamber;
a top section disposed on the bottom section comprising:
an extensible right rear chamber disposed towards a right end of the top section;
an extensible left rear chamber disposed towards a left end of the top section, an extensible front chamber disposed on the top section that is positioned between and spaced apart from the right rear chamber and the left rear chamber by a gap that extends downwardly through the top section that is not dimensioned to be accessible by a chin of a user, and configured to accommodate relative motion between the extensible right rear chamber, the extensible left rear chamber and the extensible front chamber, wherein the left rear chamber, the right rear chamber and the front chamber are configured to be expanded in a predetermined sequence; and
a releasable closure for closing the back opening between the right end and the left end.

2. The traction system of claim 1, wherein a cutout portion on the upper surface of the front chamber is configured to support a chin cup positioned in the cutout portion.

3. The traction system of claim 2, wherein the chin cup is generally boomerang-shaped, comprising a pair of arms converging at a point;
the point is disposed at the front end of the collar; and
the chin cup is sized and dimensioned such that the point is positioned under the chin of the user and the arms extend about halfway to the angle of a mandible of the user.

4. The traction system of claim 1, comprising a temporo-mandibular joint spacer configured to engage a portion of the dentition of the user and operable to form a fulcrum positioned between the front and the back of the collar to at least partially reduce a force on a temporo-mandibular joint of the user.

5. The traction system of claim 4, wherein the temporo-mandibular joint spacer comprises an inner wall, an upper wall, and an outer wall defining a channel, wherein the channel is configured to at least partially engage a biting surface of at least one of molars and premolars of the user.

6. The traction system of claim 1, wherein the releasable closure comprises a plurality of flexible straps and corresponding pegs, wherein:
each peg comprises a shank and an enlarged head;
each strap comprises:
a first end and a second end;
a plurality of openings extending through the strap and extending along the strap from the first end toward the second end, wherein
each opening comprises a larger portion proximal to the second end and a smaller portion proximal to the first end;
the larger portion is sized and dimensioned to pass over the enlarged head of the peg; and
the smaller portion is sized and dimensioned to accept the shank, but not to pass over the enlarged head of the peg;
wherein
the second end of the strap is secured to one of the right end or left end of the collar, extending toward the opening, and
the corresponding peg is secured to the other of the right end or left end of the collar.

7. The traction system of claim 1, further comprising:
a first front strap securing the front chamber to the right rear chamber; and
a second front strap securing the front chamber to the left rear chamber.

8. The traction system of claim 1, further comprising:
a fluid manifold operably coupled to the bottom chamber, the right rear chamber, the left rear chamber, and the front chamber; and
a source of pressurized fluid, in fluid communication with the fluid manifold.

9. The cervical traction system of claim 1, wherein the left rear chamber, the right rear chamber and the front chamber are configured to be expanded in the predetermined ordered sequence including expansion of the left rear chamber, expansion of the right rear chamber, expansion of the front chamber, and expansion of both rear chambers, a phase-shifted variant, and a sequence including expansion of the left rear chamber, expansion of the right rear chamber, expansion of the front chamber, and expansion of both rear chambers, in reverse order.

10. The cervical traction system of claim 9, wherein the left rear chamber, the right rear chamber and the front chamber are configured to be expanded at different expansion rates.

11. The cervical traction system of claim 1, wherein the left rear chamber, the right rear chamber and the front chamber are configured to be expanded in the predetermined ordered sequence including expansion of the left rear chamber, expansion of both rear chambers, expansion of the right rear chamber, and expansion of the front chamber, a phase-shifted variant, and a sequence including expansion of the left rear chamber, expansion of the right rear chamber, expansion of the front chamber, and expansion of both rear chambers, in reverse order.

12. The cervical traction system of claim 11, wherein the left rear chamber, the right rear chamber and the front chamber are configured to be expanded at different expansion rates.

13. A cervical traction system including a multi-chambered collar, comprising:
a right side and a left side extending from a front to a back and defining an opening at the back configured to admit a neck portion of the user;
a releasable closure configured to extend across the opening to secure the collar to the user;
a bottom section including an extensible bottom chamber;
a top section disposed on the bottom section that comprises:
an extensible right rear chamber disposed towards a right end of the top section;
an extensible left rear chamber disposed towards a left end of the top section;
an extensible front chamber disposed on the top section that is positioned between and spaced apart from the right rear chamber and the left rear chamber to define gaps extending downwardly through the top section and having respective widths not dimensioned to be accessible by a chin of a user, wherein the gaps are configured to accommodate a relative motion between the extensible right rear chamber, the extensible left rear chamber and the extensible front chamber, further wherein the extensible right rear chamber, the extensible left rear chamber and the extensible front chamber are configured to be expanded according to a predetermined extension sequence; and
fastening devices extending across the gaps and coupling the front chamber to the right rear chamber and coupling the front chamber to the left rear chamber to limit an expansion of the respective widths.

14. The system of claim 13, wherein the fastening devices include members having opposing ends configured to be rotatably coupled to the front chamber, the right rear chamber and the left rear chamber.

15. The system of claim 14, wherein the members include relatively non-extensible members, and the opposing ends are rotatably coupled to the front chamber, the right rear chamber and the left rear chamber using rivets.

16. The system of claim 13, wherein the fastening devices include at least one of adhesives, laces, hooks, stitching, screws, bolts, pins and hook and loop fasteners.

17. The cervical traction system of claim 13, wherein the extensible right rear chamber, the extensible left rear chamber and the extensible front chamber are configured to be expanded according to a predetermined extension sequence that includes expansion of the left rear chamber, expansion of the right rear chamber, expansion of the front chamber, and expansion of both rear chambers, a phase-shifted variant, and a sequence including expansion of the left rear chamber, expansion of the right rear chamber, expansion of both rear chambers, and expansion of the front chamber in reverse order.

18. The cervical traction system of claim 17, wherein the extensible right rear chamber, the extensible left rear chamber and the extensible front chamber are configured to be expanded at different expansion rates.

19. The cervical traction system of claim 13, wherein the extensible right rear chamber, the extensible left rear chamber and the extensible front chamber are configured to be expanded according to a predetermined extension sequence that includes expansion of the left rear chamber, expansion of both rear chambers, expansion of the right rear chamber, and expansion of the front chamber, a phase-shifted variant, and a sequence including expansion of the left rear chamber, expansion of the right rear chamber, expansion of the front chamber, and expansion of both rear chambers, in reverse order.

20. The cervical traction system of claim 19, wherein the extensible right rear chamber, the extensible left rear chamber and the extensible front chamber are configured to be expanded at different expansion rates.

21. A cervical traction system, comprising:
a collar configured to be removably coupled to a neck portion of a user, the collar comprising:
an extensible front member configured to engage a mandibular region of the user;
a first extensible rear member positioned adjacent the extensible front member and configured to engage a first portion of an occipital region of the user;
a second extensible rear member positioned adjacent the extensible front member and configured to engage a second portion of the occipital region, wherein the extensible front member, the first extensible rear member and the second extensible rear member are configured to be expanded according to a predetermined extension sequence, further wherein the first extensible rear member and the second extensible rear member are separated from the extensible front member by a first gap extending between the extensible front member and the first extensible rear member and a second gap extending between the extensible front member and the second extensible rear member, wherein the first gap is configured to accommodate relative movement between the first extensible rear member and the extensible front member, and the second gap is configured to accommodate relative movement of the second extensible rear member and the extensible front member, further wherein the first gap and the second gap are not dimensioned to be accessible by a chin of the user;
a first fastening device extending across the first gap and coupling the extensible front member and the first extensible rear member; and
a second fastening device extending across the second gap and coupling the extensible front member and the second extensible rear member.

22. The system of claim 21, wherein the first fastening device is rotatably coupled at respective end portions to the extensible front member and the first extensible rear member.

23. The system of claim 22, wherein at least one of the first fastening device and the second fastening device include a relatively non-extensible member.

24. The cervical traction system of claim 21, wherein the extensible front member, the first extensible rear member and the second extensible rear member are configured to be expanded according to a predetermined extension sequence that includes expansion of the left rear chamber, expansion of the right rear chamber, expansion of the front chamber, and expansion of both rear chambers, a phase-shifted variant, and a sequence including expansion of the left rear chamber, expansion of the right rear chamber, expansion of the front chamber, and expansion of both rear chambers, in reverse order.

25. The cervical traction system of claim 24, wherein the extensible front member, the first extensible rear member and the second extensible rear member are configured to be expanded at different expansion rates.

26. The cervical traction system of claim 21, wherein the extensible front member, the first extensible rear member and the second extensible rear member are configured to be expanded according to a predetermined extension sequence that includes expansion of the left rear chamber, expansion of both rear chambers, expansion of the right rear chamber, and expansion of the front chamber, a phase-shifted variant, and a sequence including expansion of the left rear chamber, expansion of the right rear chamber, expansion of the front chamber, and expansion of both rear chambers, in reverse order.

27. The cervical traction system of claim 26, wherein the extensible front member, the first extensible rear member and the second extensible rear member are configured to be expanded at different expansion rates.

28. The cervical traction system of claim 21, wherein the extensible front member, the first extensible rear member and the second extensible rear member are configured to be expanded according to a predetermined extension sequence that includes expansion of the left rear chamber, expansion of the right rear chamber, expansion of both rear chambers, and expansion of the front chamber, a phase-shifted variant, and a sequence including expansion of the left rear chamber, expansion of the right rear chamber, expansion of the front chamber, and expansion of both rear chambers, in reverse order.

29. The cervical traction system of claim 28, wherein the extensible front member, the first extensible rear member and the second extensible rear member are configured to be expanded at different expansion rates.

30. The system of claim 21, wherein the second fastening device is rotatably coupled at respective end portions to the extensible front member and the second extensible rear member.

31. The system of claim 21, wherein at least one of the first fastening device and the second fastening device includes at least one of adhesives, laces, hooks, stitching, screws, bolts, pins and hook and loop fasteners.

* * * * *